US012569435B2

(12) United States Patent　(10) Patent No.:　US 12,569,435 B2
Bidwell, III et al.　(45) Date of Patent:　Mar. 10, 2026

(54) OCULAR COMPOSITIONS AND METHODS THEREOF

(71) Applicant: University of Mississippi Medical Center, Jackson, MS (US)

(72) Inventors: Gene L. Bidwell, III, Jackson, MS (US); Eric M. George, Jackson, MS (US)

(73) Assignee: University of Mississippi Medical Center, Jackson, MS (US)

( * ) Notice: Subject to any disclaimer, the term of this patent is extended or adjusted under 35 U.S.C. 154(b) by 0 days.

(21) Appl. No.: 18/112,468

(22) Filed: Feb. 21, 2023

(65) Prior Publication Data

US 2024/0009120 A1　Jan. 11, 2024

Related U.S. Application Data

(62) Division of application No. 15/307,335, filed as application No. PCT/US2015/028348 on Apr. 29, 2015, now abandoned.

(60) Provisional application No. 61/985,808, filed on Apr. 29, 2014.

(51) Int. Cl.
| | |
|---|---|
| *A61K 9/06* | (2006.01) |
| *A61K 9/00* | (2006.01) |
| *A61K 38/10* | (2006.01) |
| *A61K 38/17* | (2006.01) |
| *A61K 38/18* | (2006.01) |
| *A61K 38/45* | (2006.01) |
| *A61K 47/64* | (2017.01) |
| *C07K 14/71* | (2006.01) |
| *C07K 14/78* | (2006.01) |

(52) U.S. Cl.
CPC .............. *A61K 9/06* (2013.01); *A61K 9/0048* (2013.01); *A61K 38/10* (2013.01); *A61K 38/1703* (2013.01); *A61K 38/179* (2013.01); *A61K 38/18* (2013.01); *A61K 38/45* (2013.01); *A61K 47/64* (2017.08); *C07K 14/78* (2013.01); *C12Y 207/10001* (2013.01); *C07K 14/71* (2013.01); *C07K 2319/10* (2013.01)

(58) Field of Classification Search
None
See application file for complete search history.

(56) References Cited

U.S. PATENT DOCUMENTS

| | | |
|---|---|---|
| 10,081,667 B2 | 9/2018 | Bidwell |
| 2010/0022455 A1* | 1/2010 | Chilkoti ................... A61P 3/04 |
| | | 536/23.4 |
| 2012/0064001 A1 | 3/2012 | Kavlie |

FOREIGN PATENT DOCUMENTS

| | | | | |
|---|---|---|---|---|
| WO | WO-2013016578 A2 * | 1/2013 | ............. | A61K 38/18 |
| WO | WO-2015051001 A2 * | 4/2015 | ........... | A61K 38/005 |

OTHER PUBLICATIONS

Barleon et al. (J Biol Chem. Apr. 18, 1997;272(16): 10382-8) (Year: 1997).*
Wu et al. (J Cell Mol Med. Mar. 2010; 14(3): 528-5) (Year: 2010).*
Lai et al. (Hum Gene Ther. Jul. 1, 2001;12(10):1299-310) (Year: 2001).*
Chilkoti et al. (Curr Opin Chem Biol. Dec. 2006; 10(6): 652-657) (Year: 2006).*
Costello et al. (Pancreat Disord Ther; Suppl 4; doi:10.4172/2165-7092.S4-002) (Year: 2013).*
Hersh et al. (Clinical Infectious Diseases 2012;54(11):1677-8) (Year: 2012).*
B.K. Ambati, E. Patterson, P. Jani, C. Jenkins, E. Higgins, N. Singh, et al., Soluble vascular endothelial growth factor receptor-\ contributes to the corneal antiangiogenic barrier, Br J Ophthalmol. 91 (2007) 505-8. doi: 1 0.1136/bjo.2006.107417.
B.K. Ambati, M. Nozaki, N. Singh, A. Takeda, P.O. Jani, T. Suthar, et al., Corneal avascularity is due to soluble VEGF receptor , Nature. 443 (2006) 993-7. doi: I 0.1 038/nature05249.
C. Wiesmann, G. Fuh, H.W. Christinger, C. Eigenbrot, J.A. Wells, A.M. de Vos, Crystal structure at 1.7 A resolution of VEGF in complex with domain 2 of the Fit-1 receptor, Cell. 91 (1997) 695-704.
R. Akkarawongsa, A.E. Cullinan, A. Zinke!, J. Clarin, C.R. Brandt, Corneal toxicity of cell-penetrating peptides that Inhibit Herpes simplex virus entry, J Ocul Pharmacal Ther. 22 (2006) 279-89. doi: I 0.1 089/jop.2006.22.279.
M.J. Mannis, The use of antimicrobial peptides in ophthalmology: an experimental study in corneal preservation and the management of bacterial keratitis, Trans. Am. Ophthalmol. Soc. 100 (2002) 243-271.
S. Moktan, C. Ryppa, F. Kratz, D. Raucher, A thermally responsive biopolymer conjugated to an acid-sensitive derivative of paclitaxel stabilizes microtubules, arrests cell cycle, and induces apoptosis, Invest New Drugs. (201 0). doi: 1 0.1007/s I 0637-01 0-9560-x.
G.L. Bidwell, Peptides for Cancer Therapy—A Drug Development Opportunity and a Drug Delivery Challenge, Ther. Deliv. in press (2012). Ther. Deliv. 3 (2012) 609-621.

(Continued)

*Primary Examiner* — Sergio Coffa
(74) *Attorney, Agent, or Firm* — Stites & Harbison PLLC; Richard S. Myers, Jr.

(57)　ABSTRACT

Methods and pharmaceutical compositions for delivering a therapeutic agent, treating a neovascularization disorder, and treating an ocular infection include make use of a compound that includes an elastin-like polypeptide (ELP) coupled to a therapeutic agent, wherein the ELP comprises at least one repeat of the amino acid sequence VPGXG (SEQ ID NO: 1), and where the composition is suitable for ocular administration.

22 Claims, 5 Drawing Sheets

Specification includes a Sequence Listing.

(56) References Cited

OTHER PUBLICATIONS

G.L. Bidwell, E. Perkins, J. Hughes, M. Khan, J.R. James, D. Raucher, Thermally targeted delivery of a c-Myc inhibitory polypeptide inhibits tumor progression and extends survival in a rat glioma model, PLoS One. 8 (2013) e55104. doi: I 0.137I /journal.pone.00551 04.

D.W. Urry, T.M. Parker, M.C. Reid, D.C. Gowda, Biocompatibility of the bioelastic materials, poly(GVGVP) and its gamma-irradiation cross-linked matrix-summary of generic biological test results, Bioact Com pat Polym. 6 (I 99 I) 263-282.

Rincon, et al., Biocompatibility of elastin-like polymer poly(VPAVG) microparticles: in vitro and in vivo studies, Journal of Biomedical Materials Research Part A DOI 10.1002/jbm.a, pp. 343-351.

G.L. Bidwell, D. Raucher, Application of thermally responsive polypeptides directed against c-Myc transcriptional function for cancer therapy, Mol Cancer Ther. 4 (2005) 1076-85. doi: 10.1158/1535-7163.MCT-04-0253.

G.L. Bidwell, D. Raucher, Cell penetrating elastin-like polypeptides for therapeutic peptide delivery, Adv Drug Deliv Rev. 62 (2010) 1486-96. doi: 10. 1016/j.addr.2010.05.003.

G.L. Bidwell, A.A. Whittom, E. Thomas, D. Lyons, M.D. Hebert, D. Raucher, A thermally targeted peptide inhibitor of symmetrical dimethylation inhibits cancer-cell proliferation, Peptides. 31 (2010) 834-41. doi: I 0.10 16/j.peptides.20 I 0.02.007.

I. Massodi, G.L. Bidwell, D. Raucher, Evaluation of cell penetrating peptides fused to elastin-like polypeptide for drug delivery, J Control Release. 108 (2005) 396-408. doi: I 0.10 16/j.jconrel.2005.08.007.

I. Massodi, E. Thomas, D. Raucher, Application of thermally responsive elastin-like polypeptide fused to a lactoferrin-derived peptide for treatment of pancreatic cancer, Molecules. 14 (2009) 1999-2015.

S. Moktan, D. Raucher, Anticancer activity of proapoptotic peptides is highly improved by thermal targeting using elastin-like polypeptides, Int J Pept Res Ther. 18 (20 12) 227-237. doi: 10.1 007/s 10989-012-9295-y.

G.L. Bidwell, A.N. Davis, D. Raucher, Targeting a c-Myc inhibitory polypeptide to specific intracellular compartments using cell penetrating peptides, J Control Release. 135 (2009) 2-10. doi: 10.10 16/j.jconrel.2008.11.0 15.

D.W. Urry, M.M. Long, B.A. Cox, T. Ohnishi, L.W. Mitchell, M. Jacobs, The synthetic polypentapeptide of elastin coacervates and forms filamentous aggregates, Biochim Biophys Acta. 371 (1974) 597-602.

D.E. Meyer, G.A. Kong, M.W. Dewhirst, M.R. Zalutsky, A. Chilkoti, Targeting a Genetically Engineered Elastin-like Polypeptide to Solid Tumors by Local Hyperthermia, Cancer Res. 61 (2001 ) 1548-1554.

D.E. Meyer, B.C. Shin, G.A. Kong, M.W. Dewhirst, A. Chilkoti, Drug targeting using thermally responsive polymers and local hyperthermia, J Control Release. 74 (2001) 213-24.

G.L. Bidwell, E. Perkins, D. Raucher, A thermally targeted c-Myc inhibitory polypeptide inhibits breast tumor growth, Cancer Lett. 319 (2012) 136-43. doi: 10.10 16/j .canlet.20 II.I2.042.

G.L. Bidwell, I. Fokt, W. Priebe, D. Raucher, Development of elastin-like polypeptide for thermally targeted delivery of doxorubicin, Biochem Pharmacol. 73 (2007) 620-31.

G.L. Bidwell, A.N. Davis, I. Fokt, W. Priebe, D. Raucher, A thermally targeted elastin-like polypeptide-doxorubicin conjugate overcomes drug resistance, Invest New Drugs. 25 (2007) 313-26.

I. Massodi, G.L. Bidwell, A. Davis, A. Tausend, K. Credit, M. Flessner, et al., Inhibition of ovarian cancer cell metastasis by a fusion polypeptide Tat-ELP, Clin Exp Metastasis. 26 (2009) 251--60. doi:I0.1007/sI0585-009-9237-z.

S. Moktan, E. Perkins, F. Kratz, D. Raucher, Thermal targeting of an acid-sensitive doxorubicin conjugate of elastin-like polypeptide enhances the therapeutic efficacy compared with the parent compound in vivo, Mol Cancer Ther. II (2012) 1547-56. doi: 10.1158/1535/7163.MCT-11-0998.

L. Walker, E. Perkins, F. Kratz, D. Raucher, Cell penetrating peptides fused to a thermally targeted biopolymer drug carrier improve the delivery and antitumor efficacy of an acid-sensitive doxorubicin derivative, Int J Pharm. 436 (20 12) 825-32. doi: I 0.10 I6/j.ijpharm.20 12.07.043.

S.M. Hearst, L.R. Walker, Q. Shao, M. Lopez, D. Raucher, P.J. Vig, The design and delivery of a thermally responsive peptide to inhibit S I OOB-mediated neurodegeneration, Neuroscience. 197 (20 1 I) 369-80. doi: I 0. I 0 16/j .neuroscience.20 I 1.09.025.

S.S. Amruthwar, A.V. Janorkar, Preparation and characterization of elastin-like polypeptide scaffolds for local delivery of antibiotics and proteins, J Mater Sci Mater Med. 23 (201 2) 2903-12. doi: I 0.1 007/s I 0856-012-4749-5.

Iriyama, et al., Gene Transfer Using Micellar Nanovectors Inhibits Corneal Neovascularization In Vivo; Cornea; vol. 30, No. 12, Dec. 2011; pp. 1423-1427.

Gehlbach, et al., Periocular Gene Transfer of sFlt-1 Suppresses Ocular Neovascularization and Vascular Endothelial Growth Factor-Induced Breakdown of the Blood-Retinal Barrier; Human Gene Therapy, (Jan. 20, 2003) 14:129-141.

M.H. Dastjerdi, Z. Sadrai, D.R. Saban, Q. Zhang, R. Dana, Corneal penetration of topical and subconjunctival bevacizumab, Invest Ophthalmol Vis Sci. 52 (2011) 8718-23. doi:I 0.1167 /iovs.II-787 I.

Srivastava, et al., Elastin-like recombinamers as substrates for retinal pigment epithelial cell growth, Journal of Biomedical Materials Research A I Jun. 1, 2011 vol. 97A, Issue 3, pp. 243-250.

Singh, et al., Bioactive substrates for human retinal pigment epithelial cell growth from elastin-like recombinamers, Journal of Biomedical Materials Research A, 2013, pp. 639-646.

Wang et al., Protein polymer nanoparticles engineered as chaperones protect against apoptosis in human retinal bigment epithelial cells, J Control Release. Oct. 10, 2014; 191: 4-14. doi:10.1016/j.jconrel.2014.04.028.

Wang, et al., A thermo-responsive protein treatment for dry eyes, J Control Release. Feb. 10, 2015; 199: 156-167. doi:10.1016/j.jconrel.2014.11.016.

Hisueh, et al., Tear-mediated delive, ry of nanoparticles through transcytosis of the lacrimal gland, J Control Release. Jun. 28, 2015; 208: 2-13. doi:10.1016/j.jconrel.2014.12.017.

Wang, et al., Lacritin-mediated regeneration of the corneal epithelia by protein polymer nanoparticles, J Mater Chem B Mater Biol Med. Dec. 14, 2014; 2(46): 8131-8141. doi:10.1039/C4TB00979G.

Lawrence (Cold Spring Harb Perspect Biol. Dec. 2009; 1(6): a001651) (Year: 2009).

Bae et al. (Journal of Controlled Release 122 (2007) 16-23) (Year: 2007).

* cited by examiner

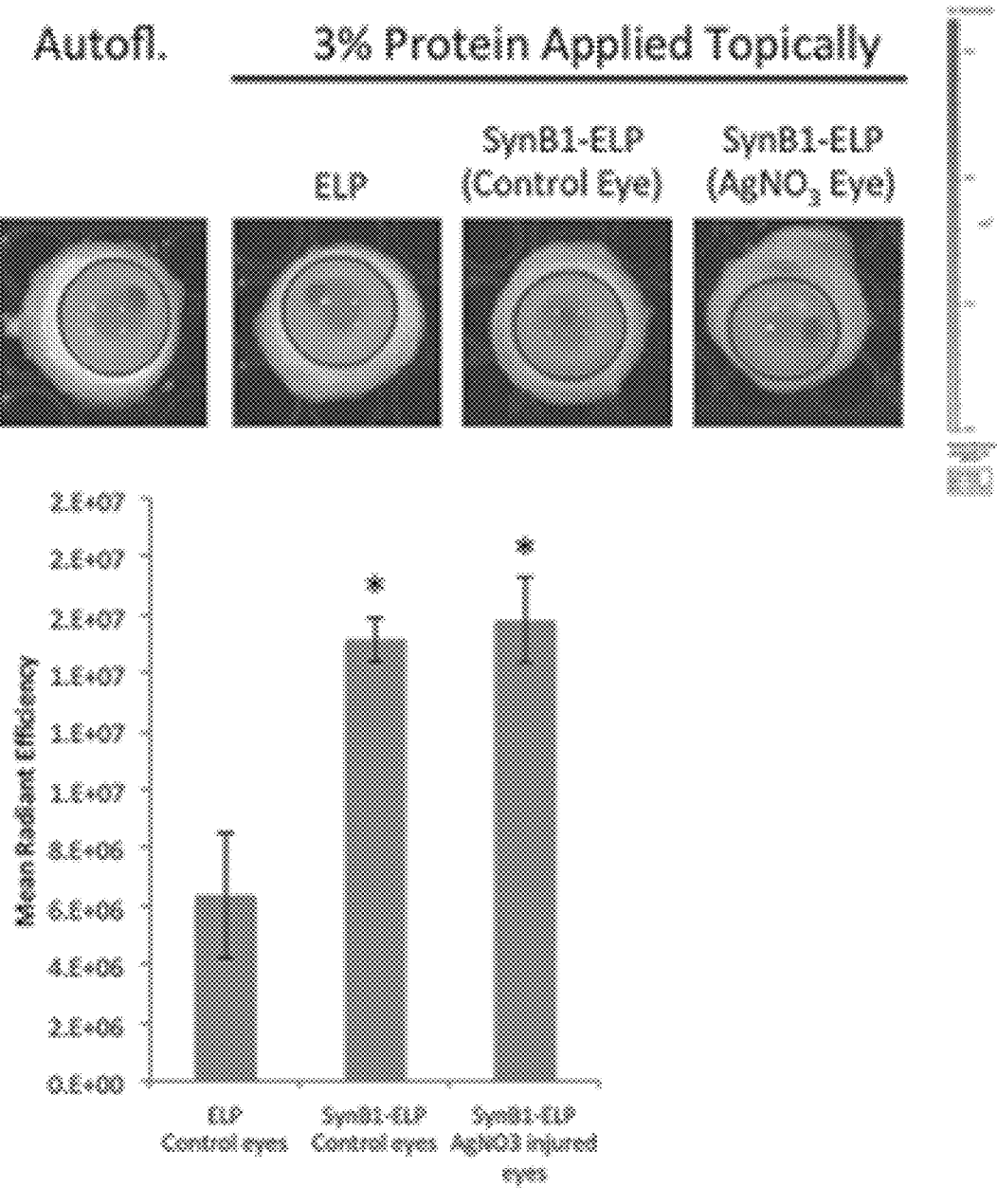
Figure 4 (Con't)

ELP      Saline      SynB1-
ELP      Saline

Protein Concentration (µg/mL)

ELP      SynB1-ELP

Saline      ELP      SynB1-ELP

ELP-sFlt

Input      ELP      Ig2-3

VEGF

SEQUENCE LISTING

```
Sequence total quantity: 17
SEQ ID NO: 1            moltype = AA  length = 5
FEATURE                 Location/Qualifiers
REGION                  1..5
                        note = xaa comprises an amino acid and does not include
                        proline
source                  1..5
                        mol_type = protein
                        organism = synthetic construct
SEQUENCE: 1
VPGXG                                                                   5

SEQ ID NO: 2            moltype = AA  length = 80
FEATURE                 Location/Qualifiers
REGION                  1..80
```

```
                          note = n repeats of the below sequence, wherein n is about
                           1 to about 100
source                    1..80
                          mol_type = protein
                          organism = synthetic construct
SEQUENCE: 2
VGVPGAGVPG GGVPGAGVPG GGVPGAGVPG GGVPGAGVPG GGVPGAGVPG GGVPGAGVPG  60
GGVPGAGVPG GGVPGAGVPG                                             80

SEQ ID NO: 3             moltype = AA  length = 40
FEATURE                  Location/Qualifiers
REGION                   1..40
                         note = n repeat of the below sequence, wherein n is about 1
                          to about 20
source                   1..40
                         mol_type = protein
                         organism = synthetic construct
SEQUENCE: 3
VGVPGAGVPG GGVPGAGVPG GGVPGAGVPG GGVPGAGVPG                          40

SEQ ID NO: 4             moltype = AA  length = 10
FEATURE                  Location/Qualifiers
REGION                   1..10
                         note = n repeats of the below sequence, wherein n is about
                          8 to about 160
source                   1..10
                         mol_type = protein
                         organism = synthetic construct
SEQUENCE: 4
VGVPGGGVPG                                                          10

SEQ ID NO: 5             moltype = AA  length = 10
FEATURE                  Location/Qualifiers
REGION                   1..10
                         note = n repeats of the below sequence, wherein n is about
                          8 to about 160
source                   1..10
                         mol_type = protein
                         organism = synthetic construct
SEQUENCE: 5
VGVPGSGVPG                                                          10

SEQ ID NO: 6             moltype = AA  length = 10
FEATURE                  Location/Qualifiers
REGION                   1..10
                         note = n repeats of the below sequence, wherein n is about
                          8 to about 160
source                   1..10
                         mol_type = protein
                         organism = synthetic construct
SEQUENCE: 6
VGVPGHGVPG                                                          10

SEQ ID NO: 7             moltype = AA  length = 10
FEATURE                  Location/Qualifiers
REGION                   1..10
                         note = n repeats of the below sequence, wherein n is about
                          8 to about 160
source                   1..10
                         mol_type = protein
                         organism = synthetic construct
SEQUENCE: 7
VGVPGVGVPG                                                          10

SEQ ID NO: 8             moltype = AA  length = 10
FEATURE                  Location/Qualifiers
REGION                   1..10
                         note = n repeats of the below sequence, wherein n is about
                          8 to about 160
source                   1..10
                         mol_type = protein
                         organism = synthetic construct
SEQUENCE: 8
VGVPGLGVPG                                                          10

SEQ ID NO: 9             moltype = AA  length = 10
FEATURE                  Location/Qualifiers
REGION                   1..10
                         note = n repeats of the below sequence, wherein n is about
```

```
                          8 to about 160
source                    1..10
                          mol_type = protein
                          organism = synthetic construct
SEQUENCE: 9
VGVPGIGVPG                                                            10

SEQ ID NO: 10             moltype = AA  length = 1338
FEATURE                   Location/Qualifiers
REGION                    1..1338
                          note = an amino acid sequence of sFlt-1 protein
source                    1..1338
                          mol_type = protein
                          organism = synthetic construct
SEQUENCE: 10
MVSYWDTGVL LCALLSCLLL TGSSSGSKLK DPELSLKGTQ HIMQAGQTLH LQCRGEAAHK  60
WSLPEMVSKE SERLSITKSA CGRNGKQFCS TLTLNTAQAN HTGFYSCKYL AVPTSKKKET  120
ESAIYIFISD TGRPFVEMYS EIPEIIHMTE GRELVIPCRV TSPNITVTLK KFPLDTLIPD  180
GKRIIWDSRK GFIISNATYK EIGLLTCEAT VNGHLYKTNY LTHRQTNTII DVQISTPRPV  240
KLLRGHTLVL NCTATTPLNT RVQMTWSYPD EKNKRASVRR RIDQSNSHAN IFYSVLTIDK  300
MQNKDKGLYT CRVRSGPSFK SVNTSVHIYD KAFITVKHRK QQVLETVAGK RSYRLSMKVK  360
APPSPEVVWL KDGLPATEKS ARYLTRGYSL IIKDVTEEDA GNYTILLSIK QSNVFKNLTA  420
TLIVNVKPQI YEKAVSSFPD PALYPLGSRQ ILTCTAYGIP QPTIKWFWHP CNHNHSEARC  480
DFCSNNEESS ILDADSNMGN RIESITQRMA IIEGKNKMAS TLVVADSRIS GIYICIASNK  540
VGTVGRNISF YITDVPNGFH VNLEKMPTEG EDLKLSCTVN KFLYRDVTWI LLRTVNNRTM  600
HYSISKQKMA ITKEHSITLN LTIMNVSLQD SGTYACRARN VYTGEEILQK KEITIRDQEA  660
PYLLRNLSDH TVAISSSTTL DCHANGVPEP QITWFKNNHK IQQEPGIILG PGSSTLFIER  720
VTEEDEGVYH CKATNQKGSV ESSAYLTVQG TSDKSNLELI TLTCTCVAAT LFWLLLTLFI  780
RKMKRSSSEI KTDYLSIIMD PDEVPLDEQC ERLPYDASKW EFARERLKLG KSLGRGAFGK  840
VVQASAFGIK KSPTCRTVAV KMLKEGATAS EYKALMTEDL ILTHIGHHLN VVNLLGACTK  900
QGGPLMVIVE YCKYGNLSNY LKSKRDLFFL NKDAALHMEP KKEKMEPGLE QGKKPRLDSV  960
TSSESFASSG PQEDKSLSDV EEEEDSDGFY KEPITMEDLI SYSFQVARGM EFLSSRKCIH  1020
RDLAARNILL SENNVVKICD FGLARDIYKN PDYVRKGDTR LPLKWMAPES IFDKIYSTKS  1080
DVWSYGVLLW EIFSLGGSPY PGVQMDEDFC SRLREGMRMR APEYSTPEIY QIMLDCWHRD  1140
PKERPRFAEL VEKLGDLLQA NVQQDGKDYI PINAILTGNS GFTYSTPAFS EDFFKESISA  1200
PKFNSGSSDD VRYVNAFKFM SLERIKTFEE LLPNATSMFD DYQGDSSTLL ASPMLKRFTW  1260
TDSKPKASLK IDLRVTSKSK ESGLSDVSRP SFCHSSCGHV SEGKRRFTYD HAELERKIAC  1320
CSPPPDYNSV VLYSTPPI                                                   1338

SEQ ID NO: 11             moltype = AA  length = 296
FEATURE                   Location/Qualifiers
REGION                    1..296
                          note = an amino acid sequence of sFlt-1 Ig-like domains 1,
                           2 and 3
source                    1..296
                          mol_type = protein
                          organism = synthetic construct
SEQUENCE: 11
PELSLKGTQH IMQAGQTLHL QCRGEAAHKW SLPEMVSKES ERLSITKSAC GRNGKQFCST  60
LTLNTAQANH TGFYSCKYLA VPTSKKKETE SAIYIFISDT GRPFVEMYSE IPEIIHMTEG  120
RELVIPCRVT SPNITVTLKK FPLDTLIPDG KRIIWDSRKG FIISNATYKI GLLTCEATVN  180
GHLYKTNYL THRQTNTIID VQISTPRPVK LLRGHTLVLN CTATTPLNTR VQMTWSYPDE  240
KNKRASVRRR IDQSNSHANI FYSVLTIDKM QNKDKGLYTC RVRSGPSFKS VNTSVH      296

SEQ ID NO: 12             moltype = AA  length = 177
FEATURE                   Location/Qualifiers
REGION                    1..177
                          note = an amino acid sequence of sFlt-1 Ig-like domains 2
                           and 3
source                    1..177
                          mol_type = protein
                          organism = synthetic construct
SEQUENCE: 12
GRELVIPCRV TSPNITVTLK KFPLDTLIPD GKRIIWDSRK GFIISNATYK EIGLLTCEAT  60
VNGHLYKTNY LTHRQTNTII DVQISTPRPV KLLRGHTLVL NCTATTPLNT RVQMTWSYPD  120
EKNKRASVRR RIDQSNSHAN IFYSVLTIDK MQNKDKGLYT CRVRSGPSFK SVNTSVH     177

SEQ ID NO: 13             moltype = AA  length = 398
FEATURE                   Location/Qualifiers
REGION                    1..398
                          note = an amino acid sequence of PEDF
source                    1..398
                          mol_type = protein
                          organism = synthetic construct
SEQUENCE: 13
NPASPPEEGS PDPDSTGALV EEEDPFFKVP VNKLAAAVSN FGYDLYRVRS SMSPTTNVLL  60
SPLSVATALS ALSLGADERT ESIIHRALYY DLISSPDIHG TYKELLDTVT APQKNLKSAS  120
RIVFEKKLRI KSSFVAPLEK SYGTRPRVLT GNPRLDLQEI NNWVQAQMKG KLARSTKEIP  180
DEISILLLGV AHFKGQWVTK FDSRKTSLED FYLDEERTVR VPMMSDPKAV LRYGLDSDLS  240
```

-continued

```
CKIAQLPLTG SMSIIFFLPL KVTQNLTLIE ESLTSEFIHD IDRELKTVQA VLTVPKLKLS  300
YEGEVTKSLQ EMKLQSLFDS PDFSKITGKP IKLTQVEHRA GFEWNEDGAG TTPSPGLQPA  360
HLTFPLDYHL NQPFIFVLRD TDTGALLFIG KILDPRGP                          398

SEQ ID NO: 14           moltype = AA  length = 27
FEATURE                 Location/Qualifiers
REGION                  1..27
                        note = an amino acid sequence of BLP-1 peptide
source                  1..27
                        mol_type = protein
                        organism = synthetic construct
SEQUENCE: 14
GIGASILSAG KSALKGLAKG LAEHFAN                                      27

SEQ ID NO: 15           moltype = AA  length = 19
FEATURE                 Location/Qualifiers
REGION                  1..19
                        note = an amino acid sequence of parasin-1 peptide
source                  1..19
                        mol_type = protein
                        organism = synthetic construct
SEQUENCE: 15
KGRGKQGGKV RAKAKTRSS                                               19

SEQ ID NO: 16           moltype = AA  length = 23
FEATURE                 Location/Qualifiers
REGION                  1..23
                        note = an amino acid sequence of magainin-2 peptide
source                  1..23
                        mol_type = protein
                        organism = synthetic construct
SEQUENCE: 16
GIGKFLHSAG KFGKAFVGEI MKS                                          23

SEQ ID NO: 17           moltype = AA  length = 24
FEATURE                 Location/Qualifiers
REGION                  1..24
                        note = an amino acid sequence of a ranalexin peptide
source                  1..24
                        mol_type = protein
                        organism = synthetic construct
SEQUENCE: 17
FFGGLIKIVP AMIPKIFCKI TRKC                                         24
```

OCULAR COMPOSITIONS AND METHODS THEREOF

RELATED APPLICATIONS

This application is a division of U.S. patent application Ser. No. 15/307,335, filed Oct. 27, 2016, which is a national stage entry of PCT/US2015/028348, filed Apr. 29, 2015, which claims the benefit of U.S. Provisional Application Ser. No. 61/985,808 filed Apr. 29, 2014, the entire disclosures of which are incorporated herein by reference in its entirety.

REFERENCE TO SEQUENCE LISTING SUBMITTED ELECTRONICALLY

A sequence listing electronically submitted as an XML file named bidwell_11637N-140515_ST26.xml, created on Sep. 26, 2023 and having a size of 25000 bytes, is incorporated herein by reference in its entirety.

TECHNICAL FIELD

The presently-disclosed subject matter relates to compositions and methods for ocular delivery of therapeutic agents. In particular, the presently-disclosed subject matter relates to compounds comprising an elastic-like polypeptide (ELP) coupled to a therapeutic agent as well as compositions and methods thereof.

INTRODUCTION

Delivery of drugs to the eye via topical application is especially challenging. The corneal barrier consists of tight junction connected epithelial cells over a basement membrane layer that prevent the passage of large or hydrophilic molecules into the eye. Thus, treatment of numerous diseases and conditions that affect the eyes, including those for which therapeutic agents are available, can be difficult or impractical because there exists no simple and effective method for delivering therapeutic agents.

For instance, the cornea of the eye is normally an avascular environment, and maintenance of avascularity allows for optical clarity and acute vision. Both pro-angiogenic and anti-angiogenic proteins are expressed in the cornea, and maintenance of the avascular environment is dependent on a balance between them. A player in the maintenance of corneal avascularity is the expression of sFlt-1, a soluble isoform of the VEGF receptor which serves to naturally sequester VEGF. Inhibition of sFlt-1 expression is sufficient to abolish corneal avascularity in mice, but treatment is hampered by the lack of a system to deliver sFlt-1 to the eye.

On the other hand, corneal neovascularization (NV) is a pathological condition resulting from corneal injury or infection. Persistent pathological NV leads to development and accumulation of blood vessels that are immature and structurally weak, which can then lead to lipid exudation, inflammation, scarring, and ultimately, blindness. Current treatment strategies are limited to pharmacological interventions, such as steroids, NSAIDs, and anti-angiogenic growth factors, and surgical interventions, such as photodynamic therapy, laser ablation, cautery, and superficial keratectomy.

Similarly, bacterial keratitis can be a severe and sight threatening condition. Current therapy involves topical administration of antibiotics. However, this strategy is limited by poor penetration of many antibiotics into the cornea, rapid removal of the drugs by the natural formation of tears, and development of antibiotic resistance by the infecting bacteria.

Hence, there remains a need for compositions and treatment methods for administering therapeutic agents to the eye in simple, effective, and noninvasive manner.

SUMMARY

This summary describes several embodiments of the presently-disclosed subject matter, and in many cases, lists variations and permutations of these embodiments. This summary is merely exemplary of the numerous and varied embodiments. Mention of one or more representative features of a given embodiments is likewise exemplary. Such an embodiment can typically exist with or without the feature (s) mentioned; likewise, those features can be applied to other embodiments of the presently-disclosed subject matter, whether listed in this summary or not. To avoid excessive repetition, this summary does not list or suggest all possible combinations of such features.

The presently-disclosed subject matter relates to compositions and methods for ocular delivery of therapeutic agents. In particular, the presently-disclosed subject matter relates to compounds comprising an elastic-like polypeptide (ELP) coupled to a therapeutic agent as well as compositions and methods thereof.

In some embodiments of the presently-disclosed subject matter, a method of delivering a therapeutic agent to an eye is provided. In some embodiments, the method includes administering to the eye of a subject an effective amount of a compound that includes an elastin-like polypeptide (ELP) coupled to a therapeutic agent. In some embodiments, the ELP including at least one repeat of the amino acid sequence VPGXG (SEQ ID NO: 1). In some embodiments, non-limiting examples of administration methods includes topical administration, subconjunctival administration, intraocular injection. In some embodiments, the size of the ELP is configured to permit ocular penetration of the compound. In some embodiments, the ELP comprises about 5 to about 10 VPGXG sequences. In some embodiments, the ELP comprises about 10 to about 20 VPGXG sequences. In some embodiments, the ELP comprises about 20 to about 40 VPGXG sequences. In some embodiments, the ELP comprises about 40 to about 80 VPGXG sequences. In some embodiments, the X amino acid is hydrophilic which can permit stability of the compound in the ocular environment. In some embodiments, X includes Val, Ala, or Gly in a 1:8:7 ratio (e.g., SEQ ID NO:2). In some embodiments, X includes Val, Ala, or Gly in a 1:4:3 ratio (e.g., SEQ ID NO:3). In some embodiments, X includes Gly (e.g., SEQ ID NO:4). In some embodiments, X includes Ser (e.g., SEQ ID NO:5). In some embodiments, X includes His (e.g., SEQ ID NO:6). In some embodiments, X is hydrophobic to permit corneal penetration of the compound. In some embodiments, X includes Val (e.g., SEQ ID NO:7). In some embodiments, X includes Leu (e.g., SEQ ID NO:8). In some embodiments, X includes Ile (e.g., SEQ ID NO:9). In some embodiments, the therapeutic agent is linked to the ELP carrier with a cleavable linker to allow release of the therapeutic agent intraocularly.

In some embodiments of the presently disclosed subject matter, the compound further comprises a cell-penetrating peptide (CPP) coupled to the ELP. In some embodiments, the cell-penetrating peptide includes penetratin, Tat, SynB1, Bac, polyArg, MTS, Transportan, and pVEC. In some embodiments, the compound further includes an attachment site configured to couple to a therapeutic agent. In some embodiments, the attachment site includes one or more Cys residues at a N-terminus, a C-terminus, or an interior of the compound. In some embodiments, the attachment site includes one or more Lys residues at a N-terminus, a C-terminus, or an interior of the compound.

In some embodiments of the presently disclosed subject matter, the compound forms a hydrogel after topical application or intraocular injection. In some embodiments, the compound has a phase transition below the ocular temperature, wherein ocular injection or application induces phase transfer and hydrogel formation. In some embodiments, the hydrogel formation increases ocular residence time and bioavailability of the therapeutic.

In some embodiments, the presently disclosed subject matter provides a method of treating a neovascularization disorder in a subject. The method includes administering to the eye of the subject an effective amount of a compound that comprises an elastin-like polypeptide (ELP) coupled to a therapeutic agent. In some embodiments, the ELP comprises at least one repeat of the amino acid sequence VPGXG (SEQ ID NO: 1). In some embodiments, the therapeutic agent is a VEGF antagonist. In some embodiments, the therapeutic agent is a member of the sFlt-1 family, a portion of the sFlt-1 protein (e.g., SEQ ID NO:10), or a combination thereof. In some embodiments, the therapeutic agent is sFlt-1 Ig-like domains 1, 2, and 3 (SEQ ID NO:11). In some embodiments, the therapeutic agent is sFlt-1 Ig-like domains 2 and 3 (SEQ ID NO:12). In some embodiments, the therapeutic agent comprises PEDF (SEQ ID NO:13). In some embodiments, the therapeutic agent comprises an anti-inflammatory drug, an anti-inflammatory peptide, or a combination thereof. In some embodiments, the method further comprises a cell-penetrating peptide. In some embodiments, non-limiting examples of the cell penetrating peptide are penetratin, Tat, SynB1, Bac, polyArg, MTS, Transportan, POD, and pVEC.

Further provided in some embodiments of the presently disclosed subject matter, is a method of treating an ocular infection in a subject. The method includes administering to the eye of a subject an effective amount of a compound that includes an elastin-like polypeptide (ELP) coupled to a therapeutic agent. In some embodiments, the ELP includes at least one repeat of the amino acid sequence VPGXG (SEQ ID NO: 1). In some embodiments, the therapeutic agent includes a BLP-1 peptide (SEQ ID NO:14). In some embodiments, the therapeutic agent includes a parasin-1 peptide (SEQ ID NO:15). In some embodiments, the therapeutic agent includes a magainin-2 peptide (SEQ ID NO:16). In some embodiments, the therapeutic agent includes a ranalexin peptide (SEQ ID NO:17). In some embodiments, the method further includes a cell-penetrating peptide. In some embodiments, non-limiting examples of the cell-penetrating peptide includes penetratin, Tat, SynB1, Bac, polyArg, MTS, Transportan, POD, and pVEC.

The presently disclosed subject matter, in some embodiments, further provides a composition. The composition includes a compound that includes an elastin-like polypeptide (ELP) coupled to a therapeutic agent, wherein the ELP comprises at least about 5 repeats of the amino acid sequence VPGXG (SEQ ID NO: 1), and a pharmaceutically acceptable carrier for topical delivery to an eye. In some embodiments, the composition includes eye drops, an ointment, or a combination thereof. In some embodiments, the composition further includes thickening agents. In some embodiments, the thickening agents includes polyvinyl alcohol, polyethylene glycol, methyl cellulose, and/or carboxymethyl cellulose. In some embodiments, the composition further includes an agent modulating tonicity. In some embodiments, the tonicity modulating agent includes boric acid and/or sodium phosphate buffer. In some embodiments, the composition further includes a surfactant to increase corneal penetration. In some embodiments, the surfactant includes benzalkonium chloride, polysorbate 20, polysorbate 80, and/or dioctyl sodium sulpho succinate. In some embodiments, the composition further includes a buffering agent to adjust the pH of the solution. In some embodiments, the ELP comprises about 5 to about 80 VPGXG sequences. In some embodiments, the X amino acid is hydrophilic and/or hydrophobic. In some embodiments, X includes one or more of Val, Ala, and Gly in a 1:8:7 ratio (e.g., SEQ ID NO:2), Val, Ala, and Gly in a 1:4:3 ratio e.g., (SEQ ID NO:3), Gly (e.g., SEQ ID NO:4), Ser (e.g., SEQ ID NO:5), His (e.g., SEQ ID NO:6), Val (e.g., SEQ ID NO:7), Leu (e.g., SEQ ID NO:8), Ile (e.g., SEQ ID NO:9), or a combination thereof. In some embodiments, the compound further comprises a cell-penetrating peptide (CPP) coupled to the ELP. Non-limiting examples of the cell-penetrating peptide includes penetratin, Tat, SynB1, Bac, polyArg, MTS, Transportan, POD, and pVEC. In some embodiments, the compound further comprises an attachment site configured to couple to a therapeutic agent. In some embodiments, the attachment site includes one or more Cys residues. In some embodiments, the attachment site includes one or more Lys residues. In some embodiments, the attachment site includes one or more Cys residues and one or more Lys residues. Non-limiting examples of the therapeutic agent include a VEGF antagonist, a member of the sFlt-1 family, a portion of the sFlt-1 protein (SEQ ID NO:10), sFlt-1 Ig-like domains 1, 2, and 3 (SEQ ID NO:11), PEDF (SEQ ID NO:13), an anti-inflammatory drug and/or peptide, a BLP-1 peptide (SEQ ID NO:14), a parasin-1 peptide (SEQ ID NO:15), a magainin-2 peptide (SEQ ID NO:16), and a ranalexin peptide (SEQ ID NO:17).

The presently disclosed subject matter, in some embodiments, provides a compound. In some embodiments, the compound includes an elastin-like polypeptide (ELP) coupled to a therapeutic agent, wherein the ELP comprising at least one repeat of the amino acid sequence VPGXG (SEQ ID NO: 1). In some embodiments, the ELP is about 16 to about 160 VPGXG (SEQ ID NO: 1) sequences. In some embodiments, the X amino acid is hydrophilic. In some embodiments, the X amino acid is hydrophobic. In some embodiments, the X amino acid is hydrophilic, hydrophobic, or a combination thereof. In some embodiments, X includes one or more of Val, Ala, and Gly in a 1:8:7 ratio (e.g., SEQ ID NO:2), Val, Ala, and Gly in a 1:4:3 ratio (e.g., SEQ ID NO:3), Gly (e.g., SEQ ID NO:4), Ser (e.g., SEQ ID NO:5), His (e.g., SEQ ID NO:6), Val (e.g., SEQ ID NO:7), Leu (e.g., SEQ ID NO:8), Ile (e.g., SEQ ID NO:9), or any combination thereof. In some embodiments, the compound further comprises a cell-penetrating peptide (CPP) coupled to the ELP. Non-limiting examples of the cell-penetrating peptide include penetratin, Tat, SynB1, Bac, polyArg, MTS, Transportan, POD, and pVEC. In some embodiments, the compound further comprises an attachment site configured to couple to a therapeutic agent. In some embodiments, the attachment site is one or more Cys residues. In some embodiments, the attachment site is one or more Lys residues. In some embodiments, the attachment site is one or more Cys residues and one or more Lys residues. In some embodiments, the therapeutic agent includes one or more of a VEGF antagonist, a member of the sFlt-1 family, a portion of the sFlt-1 protein (SEQ ID NO:10), sFlt-1 Ig-like domain 1, 2, and 3 (SEQ ID NO:11), PEDF (SEQ ID NO:13), an anti-inflammatory drug and/or peptide, a BLP-1 peptide (SEQ ID NO:14), a parasin-1 peptide (SEQ ID NO:15), a magainin-2 peptide (SEQ ID NO:16), and a ranalexin peptide (SEQ ID NO:17).

BRIEF DESCRIPTION OF THE SEQUENCE LISTING

SEQ ID NO:1 is an amino acid sequence, VPGXG, where X can be any amino acid except proline.

SEQ ID NO: 2 is a ELP, including a series of VPGXG (SEQ ID NO:1) units in which X is Val, Ala, and Gly in 1:8:7 ratio; SEQ ID NO: 2 can be repeated in a single ELP from 1 to about 10 times (n is 1 to about 10).

SEQ ID NO: 3 is a ELP, including a series of VPGXG (SEQ ID NO:1) units in which X is Val, Ala and Gly in 1:4:3 ratio; SEQ ID NO: 3 can be repeated in a single ELP from about 1 to about 20 times (n is 1 to about 20).

SEQ ID NO: 4 is a ELP sequence of about 8 to about 160 repeats of amino acid sequence (VG VPGGG VPG)$_n$, where n is about 8 to about 160.

SEQ ID NO: 5 is a ELP sequence of about 8 to about 160 repeats of amino acid sequence (VG VPGSG VPG)$_n$, where n is about 8 to about 160.

SEQ ID NO: 6 is a ELP sequence of about 8 to about 160 repeats of amino acid sequence (VG VPGHG VPG)$_n$, where n is about 8 to about 160.

SEQ ID NO: 7 is a ELP sequence of about 8 to about 160 repeats of amino acid sequence (VG VPGVG VPG)$_n$, where n is about 8 to about 160.

SEQ ID NO: 8 is a ELP sequence of about 8 to about 160 repeats of amino acid sequence (VG VPGLG VPG)$_n$, where n is about 8 to about 160.

SEQ ID NO: 9 is a ELP sequence of about 8 to about 160 repeats of amino acid sequence (VG VPGIG VPG)$_n$, where n is about 8 to about 160.

SEQ ID NO: 10 is an amino acid sequence of sFlt-1 protein.

SEQ ID NO: 11 is an amino acid sequence of sFlt-1 Ig-like domains 1, 2 and 3.

SEQ ID NO: 12 is an amino acid sequence of sFlt-1 Ig-like domains 2 and 3.

SEQ ID NO: 13 is an amino acid sequence of PEDF.

SEQ ID NO: 14 is an amino acid sequence of BLP-1 peptide.

SEQ ID NO: 15 is an amino acid sequence of parasin-1 peptide.

SEQ ID NO: 16 is an amino acid sequence of magainin-2 peptide.

SEQ ID NO: 17 is an amino acid sequence of a ranalexin peptide.

DESCRIPTION OF EXEMPLARY EMBODIMENTS

Figure 1:
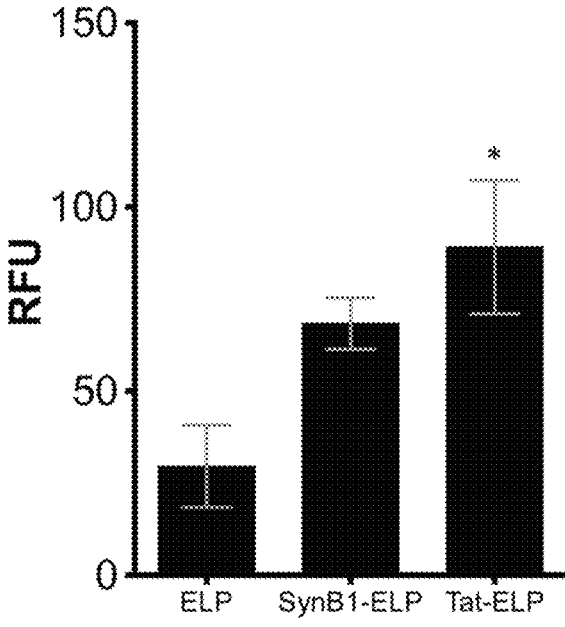
FIG. 1 illustrates uptake of Proteins in Corneal Epithelial Cells. HCE cells were exposed to 10 NM fluorescently labeled ELP, SynB1-ELP, or Tat-ELP. 24 h after exposure, protein levels were determined by flow cytometry. Bars, sem.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes compounds that can be utilized to administer a therapeutic agent to an eye of a subject. Embodiments of the compounds can cross the corneal barrier. Some embodiments can also penetrate and/or accumulate in the corneal stroma and other structures of the eye. In some embodiments the compounds comprise an elastin-like polypeptide (ELP) that is coupled to a therapeutic agent. Furthermore, in some embodiments the compound can further comprise a cell-penetrating peptide (CPP) coupled to the ELP. In some embodiments the present compounds can be utilized as a drug delivery vector that is capable of crossing the corneal barrier.

The terms "polypeptide", "protein", and "peptide", which are used interchangeably herein, refer to a polymer of the protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide", and "peptide" are used interchangeably herein when referring to a gene product. Thus, exemplary polypeptides include gene products, naturally occurring proteins, homologs, orthologs, paralogs, fragments and other equivalents, variants, and analogs of the foregoing. Furthermore, the term "fusion polypeptide" is used herein to generally refer to a polypeptide formed from two or more distinct polypeptides.

The term "therapeutic agent" and the like is used herein to refer to substances that can alter, inhibit, active, catalyze, or otherwise affect a biological or chemical event in a subject. In some embodiments a therapeutic agent has the effect of treating a disease, condition, or disorder in a subject, and possibly in the eye of a subject. Exemplary active agents include, but are not limited to, enzymes, organic catalysts, ribozymes, organometallics, proteins, glycoproteins, peptides, polyamino acids, antibodies, nucleic acids, steroidal molecules, antibiotics, antibacterial agents, anti-inflammatory agents, antivirals, antimycotics, anticancer agents, analgesic agents, antirejection agents, immunosuppressants, cytokines, carbohydrates, oleophobics, lipids, pharmaceuticals (i.e., drugs; including small molecules), chemotherapeutics, and combinations thereof.

In some instances the compound is for treating a neovascularization disorder, and the therapeutic agent includes one or more of VEGF antagonist, a member of the sFlt-1 family, a portion of the sFlt-1 protein (SEQ ID NO: 10), sFlt-1 Ig-like domain 1, 2, and 3 (SEQ ID NO:11), and PEDF (SEQ ID NO:13).

In this respect, the sFlt-1 protein is a splice variant of the VEGF receptor that consists of its soluble extracellar portion. sFlt is made up of 7 immunoglobulin-like (Ig) domains which are responsible for VEGF binding. The first three domains (sFlt Ig1-3) are capable of binding VEGF with an affinity 2-fold lower than the full length protein, and domains 2-3 (sFlt Ig2-3) can bind with 4.5-fold lower affinity than the full protein. Given the small size of the sFlt Ig1-3 and sFlt Ig2-3 domains, about 20 kDa and 30 kDa, respectively, and their high affinity for VEGF, compounds comprising therapeutic agents with such sFlt domains could be useful in topical applications for treatment of corneal neovascularization disorder.

Furthermore, the antibacterial agents can include antibacterial peptides, which are a class of naturally occurring short peptides that have bacteriocidal or bacteriostatic properties. They can be derived mostly from frogs and insects and the like, and some are found in cows and humans and the like. Antimicrobial peptides often have a positive charge and function by binding bacterial membranes and inducing pore formation or cell lysis. Antibacterial peptides are relatively less susceptible to induction of resistance in the target microorganisms. Exemplary antibacterial peptides include, but are not limited to, magainin-2, parasin-1, BLP-1, and ranalexin.

In some instances the compound is for treating a ocular infection, and the therapeutic agent includes one or more of BLP-1 peptide (SEQ ID NO:14), a parasin-1 peptide (SEQ ID NO:15), a magainin-2 peptide (SEQ ID NO:16), and a ranalexin peptide (SEQ ID NO:17).

In some embodiments, the compound includes reactive sites for attachment of therapeutic agents, with or without a cleavable linker. A non-limiting list of potential therapeutic agents that can be provided with the present compounds include those listed in the following tables.

TABLE 1

Partial list of pharmaceuticals that can be coupled to a ELP for delivery.
Ocular Pharmaceuticals

| | | |
|---|---|---|
| Ketorolac | Naphazoline | Lidocaine |
| Pemirolast | Brimonidine | Azelastine |
| Azithromycin | Bepotastine | Besifloxacin |
| Betaxon | Cosopt | Cysteamine |
| Difluprednate | Aflibercept | Tasimelteon |
| Ocriplasmin | Lotemax | Enoxaparin |
| Gatifloxacin | Bimatoprost | Pegaptanib |
| Ofloxacin | Dexamethasone | Levofloxacin |
| Unoprostone | Cyclosporine | Travoprost |
| Valganciclovir | Viroptic | Cidofovir |
| Verteporfin | Vitrasert | Vitravene |
| Zaditor | Tafluprost | Ganciclovir |
| Dexamethasone | Fluocinolone | Loteprednol |
| Difluprednate | Fluoromethalone | Prednisolone |
| Medrysone | Triamcinolone | Rimexolone |

TABLE 2

Partial list of peptide, protein, and antibody therapeutic
agents that can be coupled to a ELP for delivery.

| THERAPEUTIC PEPTIDES | | |
|---|---|---|
| Peptide Name | Protein of origin | Amino Acids |
| PNC-2 | Ras | 96-110 |
| PNC-7 | Ras | 35-47 |
| PNC-25 | SOS | 994-1004 |
| n.s.* | Raf | 97-110 |
| n.s.* | Raf | 143-150 |
| n.s.* | NF1-GAP | 1121-1128 |
| SP1068 | EGFR | 1063-1073 |
| SY317 | Shc | 312-323 |
| n.s.* | MEK1 | 1-13 |
| n.s.* | GST-pi | 34-50 |
| JNKI1 | JIP1/IB1 | 153-172 |
| JNKI2 | JIP2/IB2 | 134-151 |
| I-JIP | JIP1/IB1 | 143-163 |
| TI-JIP | JIP1/IB1 | 153-163 |
| NBD | IKKβ | 735-745 |
| CC2 | NEMO | 253-287 |
| LZ | NEMO | 294-336 |
| SN50 | NF-κB p50 | 360-369 |
| pp21 | IκBα | 21-41 |
| p65-P1 | NF-κB p65 | 271-282 |
| p65-P6 | NF-κB p65 | 525-537 |

TABLE 2-continued

Partial list of peptide, protein, and antibody therapeutic
agents that can be coupled to a ELP for delivery.

| | | |
|---|---|---|
| C1 | p53 | 369-383 |
| Peptide 46 | p53 | 361-382 |
| CDB3 | 53BP2 | 490-498 |
| TIP | p53 | 12-30 |
| Super-TIP | (phage selected) | |
| PNC-27 | p53 | 12-26 |
| PNC-21 | p53 | 12-20 |
| PNC-28 | p53 | 17-26 |
| αHDM2 | p53 | 16-27 |
| Peptide 3 | p14$^{ARF}$ | 1-20 |
| H1-S6A, F8A | c-Myc | 368-381 |
| n.s.* | p21 | 17-33 |
| n.s.* | p21 | 63-77 |
| Peptide 10 | p21 | 141-160 |
| W10 | p21 | 139-164 |
| Peptide 6 | p16 | 84-103 |
| Peptide 5a | p27 | Modified from 30-34 |
| C4 | cyclin A | 285-306 |
| n.s.* | E2F | 87-64 |
| n.s.* | Rb | 864-880 |
| Akt-in | TCL1 | 10-24 |
| Peptide2 | FKHRL1 | 16-24 |
| n.s.* | Bak | 72-87 |
| TO4 | Bax | 52-72 |
| n.s.* | Bax | 53-86 |
| n.s.* | Bad (mus musculis) | 140-165 |
| n.s.* | Bad | 103-127 |
| BH3 BAD | Bad | 103-123 |
| Bim | Bim | 145-165 |
| n.s.* | Bid | 84-99 |
| SAHB$_A$ | Bid | 80-101 |
| Smac-7 | Mature Smac | 1-7 |
| n.s.* | Mature Smac | 1-4 |
| dAVPI | Mature Smac | 1-4 |
| Nox2ds | NADPH oxidase 2 | 86-94 |
| Nox2 C-terminal peptide 1 | NADPH oxidase 2 | 552-570 |
| Nox2 C-terminal peptide 2 | NADPH oxidase 2 | 550-569 |
| Nox2 C-terminal peptide (with mutation at residue 500) | NADPH oxidase 2 | 491-504 |
| p22$^{phox}$ derived peptide 1 | p22$^{phox}$ | 9-23 |
| p22$^{phox}$ derived peptide 2 | p22$^{phox}$ | 31-45 |
| p22$^{phox}$ derived peptide 3 | p22$^{phox}$ | 47-61 |
| p22$^{phox}$ derived peptide 4 | p22$^{phox}$ | 85-99 |
| p22$^{phox}$ derived peptide 5 | p22$^{phox}$ | 113-127 |
| p22$^{phox}$ derived peptide 6 | p22$^{phox}$ | 82-95 |
| p22$^{phox}$ derived peptide 7 | p22$^{phox}$ | 175-194 |
| p47$^{phox}$ derived peptide 1 | p47$^{phox}$ | 323-332 |
| p47$^{phox}$ derived peptide 2 | p47$^{phox}$ | 314-331 |
| p47$^{phox}$ derived peptide 3 | p47$^{phox}$ | 315-328 |
| p47$^{phox}$ derived peptide 4 | p47$^{phox}$ | 323-332 |
| p47$^{phox}$ derived peptide 5 | p47$^{phox}$ | 334-347 |

*n.s., name not specified

Antibacterial Peptide Classes

| | | |
|---|---|---|
| Defensins | Protegrins | Tachyplesins |
| Brevinins | Indolicidin | PR-39 |
| Magainins | Cecropins | Ranalexin |
| Dermaseptin | Bimbinin | Andropin |
| Sarcotoxin | Sapecin | Apidaecin |
| Abaecin | Hymenoptaecin | Bee defensin |
| Mellitin | Attacins | Bactenecin |

THERAPEUTIC PROTEINS

| | | |
|---|---|---|
| VEGF | Insulin | β-Gluco-cerebrosidase |
| PIGF | Growth hormone | Alglucosidase-α |
| IL10 | Mecasermin | Laronidase |
| IL11 | Factor VIII | Idursulphase |
| Erythropoietin | Factor IX | Galsulphase |
| Darbepoetin | Antithormbin III | Agalsidase-β |
| G-CSF | Protein C | α-1-Proteinase inhibitor |
| Peg-G-CSF | tPA | Lipase |
| GM-CSF | Urokinase | Amylase |
| α-interferon | Factor VIIa | Adenosine deaminase |
| Interferon-α2a | Calcitonin | Albumin |
| Interferon-α2b | Teriparatide | FSH |
| Peg-Interferon-α2a | Exenatide | HCG |

TABLE 2-continued

Partial list of peptide, protein, and antibody therapeutic
agents that can be coupled to a ELP for delivery.

| | | |
|---|---|---|
| Peg-Interferon-α2b | Octreotide | Lutropin |
| Interferon-αN3 | rhBMP2 | Nesiritide |
| Interferon-β1a | rhBMP7 | Botulinum Toxin type A |
| Interferon-β1b | GnRH | Botulinum Toxin type B |
| Interferon-γ1b | KGF | Collagenase |
| IL2 | PDGF | DNAse I |
| ETAF | Trypsin | Hyaluronidase |
| Peg-Asparaginase | Bivalirudin | Papain |
| Rasbuicase | Streptokinase | L-Asparaginase |
| Lepirudin | Anistreplase | |

ANTIBODIES

| | | |
|---|---|---|
| Bevacizumab | Abatacept | Basiliximab |
| Cetuximab | Anakinra | Daclizumab |
| Panitumumab | Adalimumab | Muromonab-CD3 |
| Alemtuzumab | Etanercept | Omalizumab |
| Rituximab | Infliximab | Palivizimuab |
| Trastuzumab | Alefacept | Enfuvirtide |
| Ranibuzumab | Efalizumab | Abciximab |
| Denileukin diftitox | Natalizumab | Pegvisomant |
| Ibritumomab tiuxetan | Eculizumab | GHRH |
| Gemtuzumab ozogamicin | DPPD | Secretin |
| Tositumomab | Glucagon | TSH |
| Capromab pendetide | Indium-111-ocreotide | Satumomab pendetide |
| Arcitumomab | Nofetumomab | Apcitide |
| Imciromab pentetate | Technetium fanolesomab | Ranibizumab |

The ELP in some embodiments refers to a polypeptide comprised of at least one repeat of the amino acid sequence VPGXG, wherein X can be any amino acid except for proline (SEQ ID NO: 1). In other embodiments ELP can be of a size that permits ocular penetration of the compound, and in certain embodiments is small enough to permit ocular penetration. In some embodiments the ELP is hydrophilic so as to increase the residence time of the compound in the ocular environment, thereby increasing its stability in the ocular environment. In some embodiments the ELP and/or X is hydrophobic to permit corneal penetration of the compound. In some embodiments the ELP and/or X may have a combination of the properties described herein. For example, the ELP can comprise a hydrophilic portion and a hydrophobic portion.

Some embodiments of compounds include, but are not limited to, ELP that includes about 5, about 10, about 15, about 20, about 25, about 30, about 35, about 40, about 45, about 50, about 55, about 60, about 65, about 70, about 75, or about 80 VPGXG sequences. In some embodiments the ELP will include about 5 to about 10 VPGXG sequences, about 10 to about 20 VPGXG sequences, about 20 to about 40 VPGXG sequences, or about 40 to about 80 VPGXG sequences.

In yet other embodiments, the ELP of the present compounds are such that X includes Val, Ala, or Gly in a 1:8:7 ratio (SEQ ID NO:2) or such that X includes Val, Ala, or Gly in a 1:4:3 ratio (SEQ ID NO:3). In certain embodiments X includes Gly (SEQ ID NO:4). In certain embodiments X includes Ser (SEQ ID NO:5). In certain embodiments X includes His (SEQ ID NO:6). In certain embodiments X includes Val (SEQ ID NO:7). In certain embodiments X includes Leu (SEQ ID NO:8). In certain embodiments X includes Ile (SEQ ID NO:9).

In some embodiments, the ELP of the present compounds form transparent hydrogels on the surface of the eye or when injected into or around the eye in order to increase residence time and attain controlled release of therapeutics.

ELP is a macromolecular carrier that has several advantages. It can be an inert and biodegradable macromolecule, giving it a good pharmacokinetic profile and very low immunogenicity. Also, as opposed to chemically synthesized polymers, ELP can be expressed in and easily purified from *E. coli*. The ELP sequence can be manipulated, thereby making it relatively simple to generate chimeras of ELP fused to therapeutic agents, such as peptides. The ELP fusion can also be protease resistant and non-immunogenic, providing protection for the fused cargo from degradation and immunogenicity in vivo.

Embodiments of the presently-disclosed compounds can possess advantages by virtue of comprising ELP. In some instances ELP increases the solubility the therapeutic agents. In some instances ELP can protect labile therapeutic agents from degradation in vivo. Peptides, for instance, can be prone to degradation in blood plasma and in tissues in vivo. ELP can protect certain therapeutic agents from enzymatic degradation. In some instance ELP fusion can decrease the immunogenicity of therapeutic agents.

As described herein ELP can also be modified relatively easily to carry a therapeutic agent, such as a protein, and/or to incorporate attachment sites for coupling (i.e., binding) of therapeutic agents, such as small molecules. ELP can also be purified after recombinant expression in bacteria.

In some instances, the present compounds include an ELP that is targeted to desired tissues. For example, in some embodiments ELP and/or the compound can include a targeting agent that selectively binds and/or is attracted to a targeting substance. Target agents can include, but are not limited to, peptides, proteins, small molecules, and antibodies. In some instances the targeting agent is a CPP that can increase cell and tissue uptake, direct ELP to specific tissues, direct ELP to specific intracellular compartments, or a combination thereof.

As mentioned above, the presently-disclosed subject matter includes compounds that include an ELP coupled to a therapeutic agent, and that further comprise a cell-penetrating peptide (CPP). In some embodiments a fusion polypeptide is comprised of the ELP, the CPP, and, optionally, the therapeutic agent. Exemplary CPPs utilized in the present compounds include, but are not limited to penetratin, Tat, SynB1, Bac, polyArg, MTS, Transportan, pVEC, and peptide for ocular delivery (POD).

Some embodiments of the present compounds further include an attachment site configured to couple (e.g., electrostatically and/or covalently bind) to a therapeutic agent. In some embodiments a compounds comprises a plurality of attachment sites for one or more types of therapeutic agents. In some embodiments the attachment site includes one or more Cys residues at a N-terminus, a C-terminus, or an interior of the compound. In some embodiments the attachment site includes one or more Lys residues at a N-terminus, a C-terminus, or an interior of the compound.

The presently-disclosed subject matter includes kits comprising a compound, as disclosed herein, packaged together with a therapeutic agent. The compound can include any of the compounds described herein. The therapeutic agent can also include any of the therapeutic agents described herein. In some embodiment the kit provides a compound that includes an ELP as well as a therapeutic agent. In some embodiments the kit provides a compound that includes an ELP and a CPP as well as a therapeutic agent. The compound and therapeutic agent provided in the kit can be bound by known means before administration to a subject in need thereof. In some embodiments the kit includes two or more different therapeutic agents.

The presently-disclosed subject matter also includes compositions that comprise a compound that includes an elastin-like polypeptide (ELP) coupled to a therapeutic agent, the ELP including at least about 5 repeats of the amino acid sequence VPGXG (SEQ ID NO: 1), and that further comprise a pharmaceutically acceptable carrier for topical delivery to an eye.

The term "pharmaceutically acceptable carrier" refers to sterile aqueous or nonaqueous solutions, dispersions, suspensions or emulsions, as well as sterile powders for reconstitution into sterile solutions or dispersions just prior to use. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Depending upon the ratio of drug to polymer and the nature of the particular polymer employed, the rate of drug release can be controlled. The formulations can be sterilized, for example, by filtration through a bacterial-retaining filter or by incorporating sterilizing agents in the form of sterile solid compositions which can be dissolved or dispersed in sterile water or other sterile injectable media just prior to use. As discussed herein, the pharmaceutically acceptable carriers can include drop solutions for topical administration to the eye of a subject.

The presently-disclosed subject matter further includes a method of using the compounds described herein. In some embodiments the method comprise delivering a therapeutic agent to an eye. In specific embodiments the method comprises administering to the eye of a subject an effective amount of a compound that includes an elastin-like polypeptide (ELP) coupled to a therapeutic agent, the ELP including at least one repeat of the amino acid sequence VPGXG (SEQ ID NO: 1). In other method any of the compounds and/or compositions described herein can be administered to an eye.

In this regard, the term "administer" refers to any method of providing a compound or composition thereof to a subject. Such methods are well known to those skilled in the art and include, but are not limited to, topical administration, subconjunctival administration, intraocular injection, including intraocular injection into the aqueous or vitreous humor, and the like. In some embodiments administer refers to administration via the eye of a subject, which can include topical administration by depositing a compound or composition thereof on or near the eye. In some embodiments administration can refer to administration via topical eye drops, ointments, or other compositions. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

In this respect, one problem that can be encountered with antibody therapy in the eye after intraocular injection is that the antibodies can get out of the eye. This treatment is sometimes used for macular degeneration, for example, despite its shortcoming. The antibodies can escape the eye because they can be substrates for binding to the neonatal Fc receptor (FcRn), an antibody-binding protein expressed at the retinal—blood barrier that is responsible for active antibody transport across that barrier. However, because certain embodiments of the presently-disclosed compounds do not comprise an Fc domain, these embodiments do not bind FcRn and show lower or no systemic uptake after intraocular injection.

In some embodiments the method for administering the present compounds and compositions further include treating a disease or condition in the subject. The terms "treatment" or "treating" refer to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

Exemplary conditions and diseases that can be treated by certain methods include, but are not limited to, corneal diseases such as corneal neovascularization and keratitis, diseases of the soft tissue surrounding the eye, and diseases of the posterior eye such as macular degeneration, including wet macular degeneration. In other embodiments the disease or condition can include endophthalmitis, conjunctivitis, trachoma, periorbital cellulitis, contact-lens related infections, uveitis, *Streptococcus, Staphylococcus, Pseudomonas* infection, and the like. Other diseases and conditions include any that can be treated by a therapeutic agent that can be administered by the present compounds.

Furthermore, the term "subject" is inclusive of both human and animal subjects. Thus, veterinary uses are provided in accordance with the presently disclosed subject matter and the presently-disclosed subject matter provides methods for preventing oxidative damage in mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

In some embodiments the present compounds and compositions are administered by topical eye drops. In some embodiments the compounds can be detectable in other ocular structures, including the retina, after topical eye administration. The compounds can also accumulate in the corneal epithelium and penetrate to the stroma.

The presently-disclosed subject matter also includes methods for synthesizing the present compounds and compositions. In this respect, ELP is a thermally responsive polypeptide that can selectively form aggregates above a characteristic transition temperature ($T_t$). In some embodiments this thermally responsive nature can be exploited for purification of ELP-fused compounds by repeated centrifugation steps above and below the $T_t$, a process known as inverse transition cycling. In some embodiments, the $T_t$ can be tuned to induce hydrogel formation when administered topically to the eye or injected into or around the eye.

The presently-disclosed subject matter is further illustrated by the following specific but non-limiting examples. The following examples may include compilations of data that are representative of data gathered at various times during the course of development and experimentation related to the present invention.

EXAMPLES

Example 1

This Example characterizes the uptake of elastic-like polypeptides (ELPs) and cell-penetrating peptide ELP fusion polypeptides (CPP-ELPs) in human corneal epithelial cells (HCEs). To determine if CPPs could mediate the uptake of ELP in corneal cells, HCEs grown in culture were exposed to 10 µM fluorescently-labeled ELP, SynB1-ELP, or Tat-ELP. After 24 h incubation with the labeled proteins, the cells were detached and analyzed by flow cytometry. The mean fluorescence intensity was determined for all cells, and the fluorescence value was corrected to account for differences in labeling efficiency among the proteins. As shown in FIG. 1, ELP was detectable over autofluorescence in HCE cells, and the cellular uptake was increased 2.8-fold and 3.9-fold with SynB1 and Tat CPPs, respectively.

Figure 2:
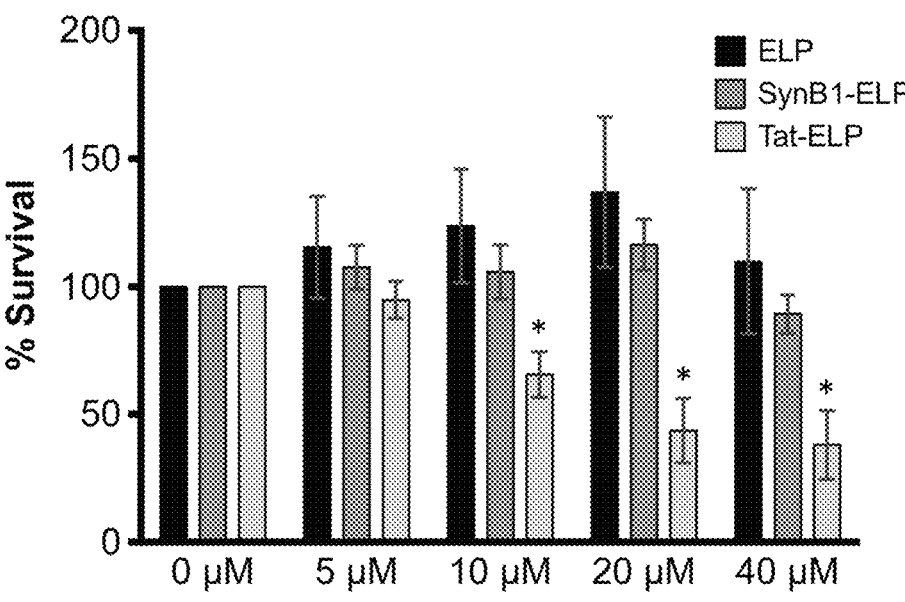
FIG. 2 shows proliferation of Corneal Epithelial Cells after exposure to ELPs. HCE cells were exposed to the indicated concentration of ELP, SynB1-ELP, or Tat-ELP for 72 h. Cell survival was assessed using the MTS cell viability assay. Bars, sem.

In addition to uptake efficiency, toxicity of ELP or CPP-ELPs to HCE cells was examined. Cells were exposed to varying concentrations of ELP, SynB1-ELP, or Tat-ELP for 72 hours, and cell number was determined using the MTS cell proliferation assay. As shown in FIG. 2, ELP and SynB1-ELP had no detectable toxicity to HCE cells at concentrations up to 40 µM. In contrast, Tat-ELP did inhibit HCE cell proliferation with an IC50 between 10 and 20 µM. These data indicate that the ELP carrier, and some CPP-ELPs, are non-toxic to corneal epithelial cells and good candidates for corneal drug delivery. They also demonstrate that some CPPs have toxicity to corneal cells, and prediction of toxicity is not possible a priori. Therefore, each candidate drug delivery vector must be made and tested individually.

Example 2

Figure 3:
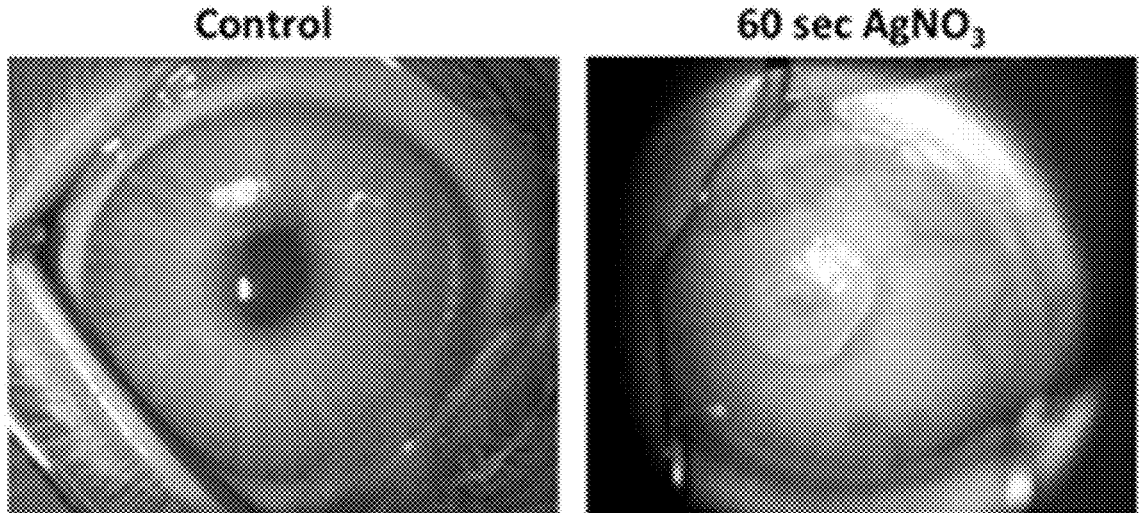
FIG. 3 illustrates establishing the Rabbit Corneal Neovascularization model. NZW rabbits were anesthetized with isoflurane and topical proparacaine, and a corneal lesion was induced using a 60 sec application of silver nitrate. Blood vessel formation 7 days after lesioning is shown.

This Example characterizes the development of a rabbit corneal neovascularization (CN) model. Rabbits were chosen for this model because the thickness of their corneal epithelial layer is similar to that of humans. New Zealand white rabbits were anesthetized with isoflurane, and a corneal burn was induced using a 60 second application of a silver nitrate cautery stick. As shown in FIG. 3, 7 days after corneal injury, the rabbits developed a neovascular response in the injured eye.

Example 3

Figure 4:
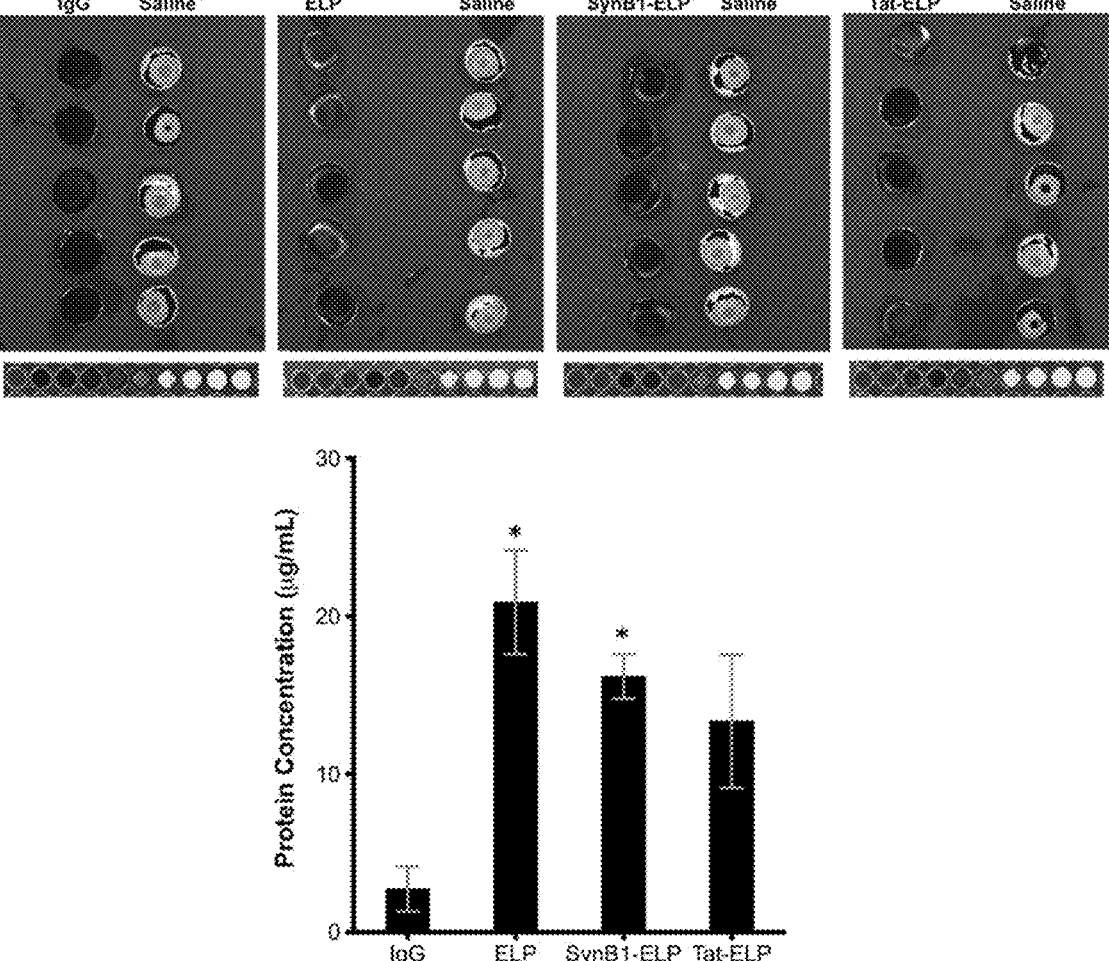
FIG. 4 shows ocular delivery of ELPs relative to IgG. A 3% solution of fluorescently labeled ELP, SynB1-ELP, Tat-ELP, or a non-specific IgG was applied topically to rabbit eyes 3 times over 6 hours. 2 h after the final administration, the eyes were removed and examined by ex vivo quantitative fluorescence to determine polypeptide levels.

This Example characterizes penetration of the corneal barrier by ELP and CPP-ELPs, and compares ELP corneal accumulation to a model antibody, immunoglobulin G (IgG). Fluorescently labeled ELP, SynB1-ELP, Tat-ELP, or IgG was applied topically via eye drops three times over 6 h in rabbits. The contralateral eye was administered saline control. 8 h after the first application, the animals were sacrificed and the eyes removed for ex vivo analysis. As shown in FIG. 4, ELP accumulated in the rabbit cornea at levels over seven-fold higher than IgG. SynB1-ELP and Tat-ELP also accumulated in the cornea much more efficiently than IgG, but the CPP-ELP corneal levels were not enhanced relative to ELP control.

Figure 5:
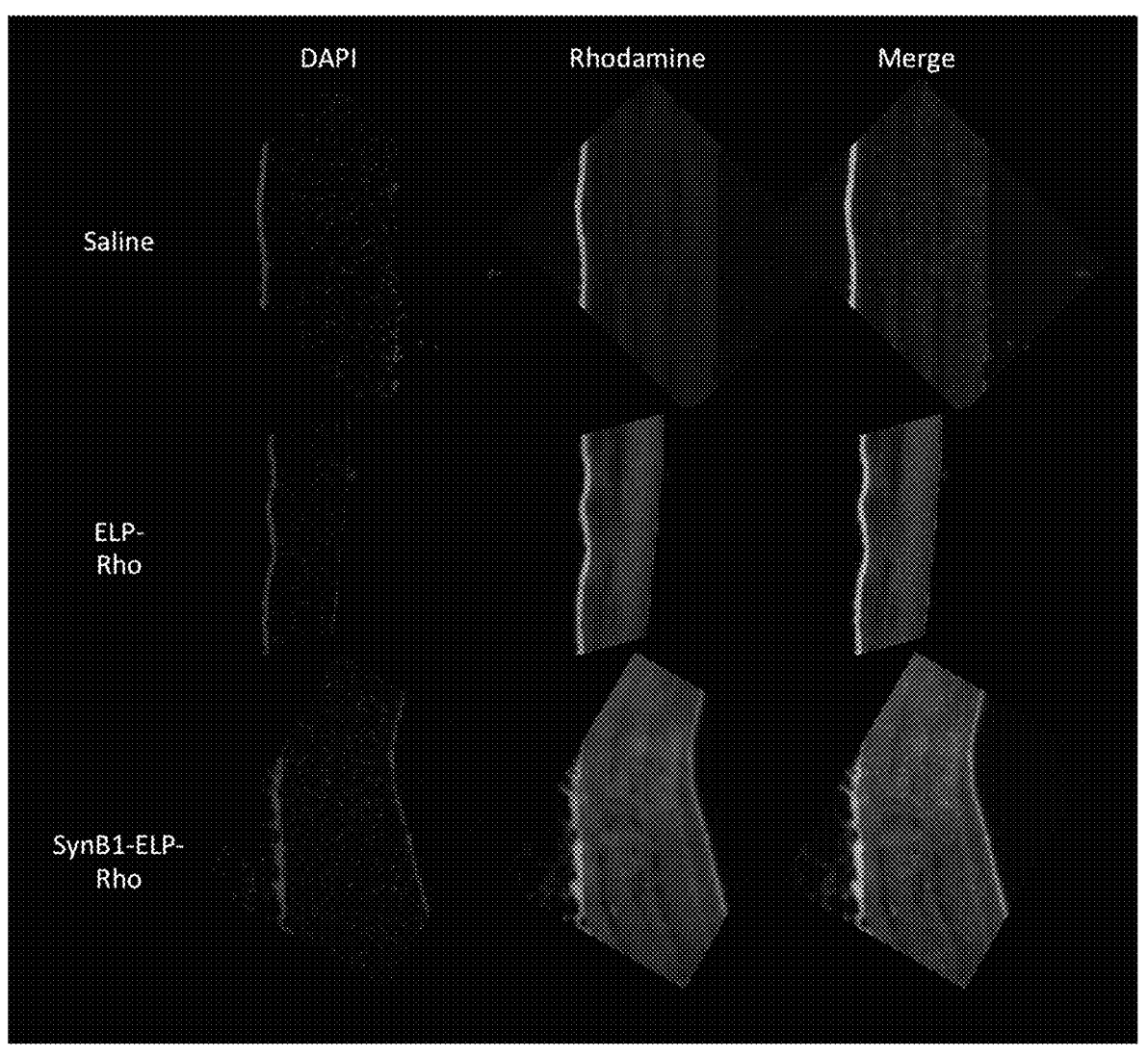
FIG. 5 shows corneal penetration of ELP or SynB1-ELP. Rabbit eyes were harvested and rapidly frozen after exposure to 3 topical applications of 3% solutions of labeled proteins of a period of 6 hours. Eyes were cut into sagittal sections using a cryomicrotome, and sections were stained with DAPI to mark cell nuclei.

After total fluorescence analysis, the eyes were frozen and cut using a cryomicrotome. Sagittal sections were used in order to visualize the cornea in cross-section. Sections were stained with DAPI to mark cell nuclei and imaged with an epifluorescence microscope. As shown in FIG. 5, the epithelial layer was brightly autofluorescent, but very little fluorescence was seen in the stroma in saline treated eyes. In contrast, both ELP and SynB1-ELP penetrated through the corneal epithelium and into the stroma. Without being bound by theory or mechanism, other CPPs may enhance the penetration of the polypeptides.

Thus, the ELP and CPP-ELP drug vectors can be effective for delivery of agents through the corneal barrier and into the stroma, the site of neovascular development.

Figures 6, 7:
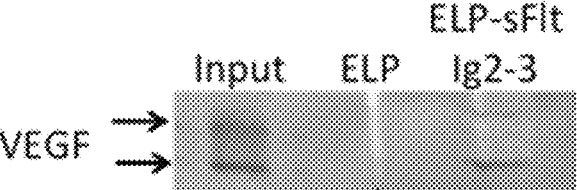
FIG. 6 shows ocular delivery of ELPs Following Increased Application Frequency. A 3% solution of fluorescently labeled ELP or SynB1-ELP was applied topically to rabbit eyes every 15 minutes for one hour, then every 30 minutes for five additional hours. 1 h after the final administration, the eyes were removed and examined by ex vivo quantitative fluorescence to determine polypeptide levels.
FIG. 7 shows ELP-sFlt Ig2-3 binding to ELP and ELP-sFlt Ig2-3 measured by SDS-PAGE and Western blot.

The frequency of dosing was increased to further test the corneal uptake and penetration of ELP and SynB1-ELP. The proteins were applied topically every 15 minutes for one hour, then every 30 minutes for five additional hours. One hour after the last application, the eyes were removed for ex vivo fluorescence analysis. As shown in FIG. 6, both ELP and SynB1-ELP accumulated in the cornea at levels much higher than autofluorescence control. SynB1-ELP levels were slightly higher than ELP levels using this dosing regimen, but the differences were not statistically significant. Eyes were also cryosectioned to examine the distribution around the eye after topical administration. This analysis revealed that both ELP and SynB1-ELP distribute around the entire eye after topical administration, and they both penetrate the corneal barrier as well as the sclera and retina. This analysis highlights the potential for using ELP-based carriers for delivery of therapeutics to all parts of the eye for treatment of many ocular disorders.

Example 4

This Example ELP-fused sFlt Ig compounds binding to VEGF. ELP-sFlt fusion proteins were made by recombinant expression in *E. coli*. As a preliminary test to insure that the sFlt Ig domain could still bind VEGF when fused to the ELP carrier, in vitro pulldown assay was performed. ELP-sFlt Ig2-3 or an ELP control lacking the sFlt peptide were incubated with purified VEGF for 1 h at 37° C. in physiological saline. Thermal precipitation of ELP and centrifugation were used to pull down ELP or ELP-sFlt Ig2-3, and the thermal precipitation was carried out two times to remove any remaining unbound protein. The precipitated proteins were separated by SDS-PAGE, transferred to nitrocellulose membranes, and the membranes were probed for VEGF by Western blot. As shown in FIG. 7, ELP-sFlt Ig2-3 was able to pull down VEGF, but the control ELP lacking the sFlt peptide did not. These results show that the sFlt peptide can maintain its ability to bind VEGF when fused to ELP.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Throughout this document, various references are mentioned. All such references are incorporated herein by reference, including the references set forth in the following list:

REFERENCE

[1] J. H. Chang, E. E. Gabison, T. Kato, D. T. Azar, Corneal neovascularization, Curr Opin Ophthalmol. 12 (2001) 242-9.

[2] B. K. Ambati, E. Patterson, P. Jani, C. Jenkins, E. Higgins, N. Singh, et al., Soluble vascular endothelial growth factor receptor-1 contributes to the corneal anti-angiogenic barrier, Br J Ophthalmol. 91 (2007) 505-8. doi:10.1136/bjo.2006.107417.

[3] B. K. Ambati, M. Nozaki, N. Singh, A. Takeda, P. D. Jani, T. Suthar, et al., Corneal avascularity is due to soluble VEGF receptor-1, Nature. 443 (2006) 993-7. doi:10.1038/nature05249.

[4] D. Gupta, C. Illingworth, Treatments for Corneal Neovascularization: A Review, Cornea. (2011). doi:10.1097/01.ico.0000396158.53170.11

[5] F. T. Wu, M. O. Stefanini, F. Mac Gabhann, C. D. Kontos, B. H. Annex, A. S. Popel, A systems biology perspective on sVEGFR1: its biological function, pathogenic role and therapeutic use, J Cell Mol Med. 14 (2010) 528-52. doi:10.1111/j.1582-4934.2009.00941.x.

[6] C. Wiesmann, G. Fuh, H. W. Christinger, C. Eigenbrot, J. A. Wells, A. M. de Vos, Crystal structure at 1.7 A resolution of VEGF in complex with domain 2 of the Flt-1 receptor, Cell. 91 (1997) 695-704.

[7] D. E. Meyer, A. Chilkoti, Purification of Recombinant Proteins by Fusion with Thermally Responsive Polypeptides, Nat. Biotechnol. 17 (1999) 1112-1115.

[8] F. Edenhofer, Protein transduction revisited: novel insights into the mechanism underlying intracellular delivery of proteins, Curr Pharm Des. 14 (2008) 3628-36.

[9] F. Madani, S. Lindberg, U. Langel, S. Futaki, A. Graslund, Mechanisms of cellular uptake of cell-penetrating peptides, J Biophys. 2011 (2011) 414729. doi: 10.1155/2011/414729.

[10] R. Akkarawongsa, A. E. Cullinan, A. Zinkel, J. Clarin, C. R. Brandt, Corneal toxicity of cell-penetrating peptides that inhibit Herpes simplex virus entry, J Ocul Pharmacol Ther. 22 (2006) 279-89. doi: 10.1089/jop.2006.22.279.

[11] M. J. Mannis, The use of antimicrobial peptides in ophthalmology: an experimental study in corneal preservation and the management of bacterial keratitis, Trans. Am. Ophthalmol. Soc. 100 (2002) 243-271.

[12] S. Moktan, C. Ryppa, F. Kratz, D. Raucher, A thermally responsive biopolymer conjugated to an acid-sensitive derivative of paclitaxel stabilizes microtubules, arrests cell cycle, and induces apoptosis, Invest New Drugs. (2010). doi:10.1007/s10637-010-9560-x.

[13] G. L. Bidwell, Peptides for Cancer Therapy—A Drug Development Opportunity and a Drug Delivery Challenge, Ther. Deliv. in press (2012).

[14] G. L. Bidwell, E. Perkins, J. Hughes, M. Khan, J. R. James, D. Raucher, Thermally targeted delivery of a c-Myc inhibitory polypeptide inhibits tumor progression and extends survival in a rat glioma model, PLoS One. 8 (2013) e55104. doi: 10.1371/journal.pone.0055104.

[15] D. W. Urry, T. M. Parker, M. C. Reid, D. C. Gowda, Biocompatibility of the bioelastic materials, poly (GVGVP) and its gamma-irradiation cross-linked matrix—summary of generic biological test results, Bioact Compat Polym. 6 (1991) 263-282.

[16] G. L. Bidwell, Peptides for cancer therapy: a drug-development opportunity and a drug-delivery challenge, Ther. Deliv. 3 (2012) 609-621.

[17] G. L. Bidwell, D. Raucher, Application of thermally responsive polypeptides directed against c-Myc transcriptional function for cancer therapy, Mol Cancer Ther. 4 (2005) 1076-85. doi:10.1158/1535-7163.MCT-04-0253.

[18] G. L. Bidwell, D. Raucher, Cell penetrating elastin-like polypeptides for therapeutic peptide delivery, Adv Drug Deliv Rev. 62 (2010) 1486-96. doi:10.1016/j.addr.2010.05.003.

[19] G. L. Bidwell, A. A. Whittom, E. Thomas, D. Lyons, M. D. Hebert, D. Raucher, A thermally targeted peptide inhibitor of symmetrical dimethylation inhibits cancer-cell proliferation, Peptides. 31 (2010) 834-41. doi: 10.1016/j.peptides.2010.02.007.

[20] I. Massodi, G. L. Bidwell, D. Raucher, Evaluation of cell penetrating peptides fused to elastin-like polypeptide for drug delivery, J Control Release. 108 (2005) 396-408. doi: 10.1016/j.jconrel.2005.08.007.

[21] I. Massodi, E. Thomas, D. Raucher, Application of thermally responsive elastin-like polypeptide fused to a lactoferrin-derived peptide for treatment of pancreatic cancer, Molecules. 14 (2009) 1999-2015.

[22] S. Moktan, D. Raucher, Anticancer activity of proapoptotic peptides is highly improved by thermal targeting using elastin-like polypeptides, Int J Pept Res Ther. 18 (2012) 227-237. doi:10.1007/s10989-012-9295-y.

[23] G. L. Bidwell, A. N. Davis, D. Raucher, Targeting a c-Myc inhibitory polypeptide to specific intracellular compartments using cell penetrating peptides, J Control Release. 135 (2009) 2-10. doi:10.1016/j.jconrel.2008.11.015.

[24] C. H. Luan, T. M. Parker, D. C. Gowda, D. W. Urry, Hydrophobicity of amino acid residues: differential scanning calorimetry and synthesis of the aromatic analogues of the polypentapeptide of elastin, Biopolymers. 32 (1992) 1251-61. doi: 10.1002/bip.360320914.

[25] C. H. Luan, T. M. Parker, K. U. Prasad, D. W. Urry, Differential scanning calorimetry studies of NaCl effect on the inverse temperature transition of some elastin-based polytetra-, polypenta-, and polynonapeptides, Biopolymers. 31 (1991) 465-75. doi:10.1002/bip.360310502.

[26] D. W. Urry, M. M. Long, B. A. Cox, T. Ohnishi, L. W. Mitchell, M. Jacobs, The synthetic polypentapeptide of elastin coacervates and forms filamentous aggregates, Biochim Biophys Acta. 371 (1974) 597-602.

[27] D. E. Meyer, G. A. Kong, M. W. Dewhirst, M. R. Zalutsky, A. Chilkoti, Targeting a Genetically Engineered Elastin-like Polypeptide to Solid Tumors by Local Hyperthermia, Cancer Res. 61 (2001) 1548-1554.

[28] D. E. Meyer, B. C. Shin, G. A. Kong, M. W. Dewhirst, A. Chilkoti, Drug targeting using thermally responsive polymers and local hyperthermia, J Control Release. 74 (2001) 213-24.

[29] M. R. Dreher, D. Raucher, N. Balu, O. Michael Colvin, S. M. Ludeman, A. Chilkoti, Evaluation of an elastin-like polypeptide-doxorubicin conjugate for cancer therapy, J Control Release. 91 (2003) 31-43.

[30] G. L. Bidwell, E. Perkins, D. Raucher, A thermally targeted c-Myc inhibitory polypeptide inhibits breast tumor growth, Cancer Lett. 319 (2012) 136-43. doi: 10.1016/j.canlet.2011.12.042.

[31] D. Y. Furgeson, M. R. Dreher, A. Chilkoti, Structural optimization of a "smart" doxorubicin-polypeptide conjugate for thermally targeted delivery to solid tumors, J Control Release. 110 (2006) 362-9.

[32] G. L. Bidwell, I. Fokt, W. Priebe, D. Raucher, Development of elastin-like polypeptide for thermally targeted delivery of doxorubicin, Biochem Pharmacol. 73 (2007) 620-31.

[33] G. L. Bidwell, A. N. Davis, I. Fokt, W. Priebe, D. Raucher, A thermally targeted elastin-like polypeptide-doxorubicin conjugate overcomes drug resistance, Invest New Drugs. 25 (2007) 313-26.

[34] I. Massodi, G. L. Bidwell, A. Davis, A. Tausend, K. Credit, M. Flessner, et al., Inhibition of ovarian cancer cell metastasis by a fusion polypeptide Tat-ELP, Clin Exp Metastasis. 26 (2009) 251-60. doi:10.1007/s10585-009-9237-z.

[35] W. Liu, J. A. MacKay, M. R. Dreher, M. Chen, J. R. McDaniel, A. J. Simnick, et al., Injectable intratumoral depot of thermally responsive polypeptide-radionuclide conjugates delays tumor progression in a mouse model, J Control Release. 144 (2010) 2-9. doi:10.1016/j.jconrel.2010.01.032.

[36] W. Liu, J. McDaniel, X. Li, D. Asai, F. G. Quiroz, J. Schaal, et al., Brachytherapy using injectable seeds that are self-assembled from genetically encoded polypeptides in situ, Cancer Res. 72 (2012) 5956-65. doi:10.1158/0008-5472.CAN-12-2127.

[37] J. A. MacKay, M. Chen, J. R. McDaniel, W. Liu, A. J. Simnick, A. Chilkoti, Self-assembling chimeric polypeptide-doxorubicin conjugate nanoparticles that abolish tumours after a single injection, Nat Mater. 8 (2009) 993-9. doi:10.1038/nmat2569.

[38] A. J. Simnick, M. Amiram, W. Liu, G. Hanna, M. W. Dewhirst, C. D. Kontos, et al., In vivo tumor targeting by a NGR-decorated micelle of a recombinant diblock copolypeptide, J Control Release. 155 (2011) 144-51. doi:10.1016/j.jconrel.2011.06.044.

[39] K. Na, S. A. Lee, S. H. Jung, J. Hyun, B. C. Shin, Elastin-like polypeptide modified liposomes for enhancing cellular uptake into tumor cells, Colloids Surf B Biointerfaces. 91 (2012) 130-6. doi:10.1016/j.colsurfb.2011.10.051.

[40] D. J. Callahan, W. Liu, X. Li, M. R. Dreher, W. Hassouneh, M. Kim, et al., Triple stimulus-responsive polypeptide nanoparticles that enhance intratumoral spatial distribution, Nano Lett. 12 (2012) 2165-70. doi:10.1021/nl300630c.

[41] J. R. McDaniel, S. R. Macewan, M. Dewhirst, A. Chilkoti, Doxorubicin-conjugated chimeric polypeptide nanoparticles that respond to mild hyperthermia, J Control Release. 159 (2012) 362-7. doi:10.1016/j.jconrel.2012.02.030.

[42] S. Moktan, E. Perkins, F. Kratz, D. Raucher, Thermal targeting of an acid-sensitive doxorubicin conjugate of elastin-like polypeptide enhances the therapeutic efficacy compared with the parent compound in vivo, Mol Cancer Ther. 11 (2012) 1547-56. doi:10.1158/1535-7163.MCT-11-0998.

[43] L. Walker, E. Perkins, F. Kratz, D. Raucher, Cell penetrating peptides fused to a thermally targeted biopolymer drug carrier improve the delivery and antitumor efficacy of an acid-sensitive doxorubicin derivative, Int J Pharm. 436 (2012) 825-32. doi:10.1016/j.ijpharm.2012.07.043.

[44] H. Betre, L. A. Setton, D. E. Meyer, A. Chilkoti, Characterization of a genetically engineered elastin-like polypeptide for cartilaginous tissue repair, Biomacromolecules. 3 (2002) 910-6.

[45] M. K. McHale, L. A. Setton, A. Chilkoti, Synthesis and in vitro evaluation of enzymatically cross-linked elastin-like polypeptide gels for cartilaginous tissue repair, Tissue Eng. 11 (2005) 1768-79. doi:10.1089/ten.2005.11.1768.

[46] M. F. Shamji, J. Chen, A. H. Friedman, W. J. Richardson, A. Chilkoti, L. A. Setton, Synthesis and characterization of a thermally-responsive tumor necrosis factor antagonist, J Control Release. 129 (2008) 179-86. doi: 10.1016/j.jconrel.2008.04.021.

[47] M. F. Shamji, L. Jing, J. Chen, P. Hwang, O. Ghodsizadeh, A. H. Friedman, et al., Treatment of neuroinflammation by soluble tumor necrosis factor receptor Type II fused to a thermally responsive carrier, J Neurosurg Spine. 9 (2008) 221-8. doi: 10.3171/SPI/2008/9/8/221.

[48] I. L. Moss, L. Gordon, K. A. Woodhouse, C. M. Whyne, A. J. Yee, A novel thiol-modified hyaluronan and elastin-like polypetide composite material for tissue engineering of the nucleus pulposus of the intervertebral disc, Spine Phila Pa 1976.36 (2011) 1022-9. doi:10.1097/BRS.0b013e3181e7b705.

[49] M. R. Dreher, M. Elas, K. Ichikawa, E. D. Barth, A. Chilkoti, G. M. Rosen, et al., Nitroxide conjugate of a thermally responsive elastin-like polypeptide for noninvasive thermometry, Med Phys. 31 (2004) 2755-62.

[50] T. H. Chen, Y. Bae, D. Y. Furgeson, Intelligent biosynthetic nanobiomaterials (IBNs) for hyperthermic gene delivery, Pharm Res. 25 (2008) 683-91.

[51] U. Conrad, I. Plagmann, S. Malchow, M. Sack, D. M. Floss, A. A. Kruglov, et al., ELPylated anti-human TNF therapeutic single-domain antibodies for prevention of lethal septic shock, Plant Biotechnol J. 9 (2011) 22-31. doi:10.1111/j.1467-7652.2010.00523.x.

[52] K. Na, J. Jung, J. Lee, J. Hyun, Thermoresponsive pore structure of biopolymer microspheres for a smart drug carrier, Langmuir. 26 (2010) 11165-9. doi:10.1021/la1013285.

[53] P. H. Blit, W. G. McClung, J. L. Brash, K. A. Woodhouse, J. P. Santerre, Platelet inhibition and endothelial cell adhesion on elastin-like polypeptide surface modified materials, Biomaterials. 32 (2011) 5790-800. doi: 10.1016/j.biomaterials.2011.04.067.

[54] S. M. Hearst, L. R. Walker, Q. Shao, M. Lopez, D. Raucher, P. J. Vig, The design and delivery of a thermally responsive peptide to inhibit S100B-mediated neurodegeneration, Neuroscience. 197 (2011) 369-80. doi: 10.1016/j.neuroscience.2011.09.025.

[55] T. H. Chen, Y. Bae, D. Y. Furgeson, G. S. Kwon, Biodegradable hybrid recombinant block copolymers for non-viral gene transfection, Int J Pharm. 427 (2012) 105-12. doi:10.1016/j.ijpharm.2011.09.035.

[56] S. S. Amruthwar, A. V. Janorkar, Preparation and characterization of elastin-like polypeptide scaffolds for local delivery of antibiotics and proteins, J Mater Sci Mater Med. 23 (2012) 2903-12. doi:10.1007/s10856-012-4749-5.

[57] S. S. Amruthwar, A. V. Janorkar, In vitro evaluation of elastin-like polypeptide-collagen composite scaffold for bone tissue engineering, Dent Mater. 29 (2013) 211-20. doi: 10.1016/j.dental.2012.10.003.

[58] K. M. Lee, G. S. Jung, J. K. Park, S. K. Choi, W. B. Jeon, Effects of Arg-Gly-Asp-modified elastin-like polypeptide on pseudoislet formation via up-regulation of cell adhesion molecules and extracellular matrix proteins, Acta Biomater. 9 (2013) 5600-8. doi:10.1016/j.actbio.2012.10.036.

[59] M. Amiram, K. M. Luginbuhl, X. Li, M. N. Feinglos, A. Chilkoti, Injectable protease-operated depots of glucagon-like peptide-1 provide extended and tunable glucose control, Proc Natl Acad Sci U A. 110 (2013) 2792-7. doi:10.1073/pnas.1214518110.

[60] A. Iriyama, T. Usui, Y. Yanagi, S. Amano, M. Oba, K. Miyata, et al., Gene transfer using micellar nanovectors inhibits corneal neovascularization in vivo, Cornea. 30 (2011) 1423-1427. doi: 10.1097/ICO.0b013e318206c893.

[61] P. Gehlbach, A. M. Demetriades, S. Yamamoto, T. Deering, W. H. Xiao, E. J. Duh, et al., Periocular gene transfer of sFlt-1 suppresses ocular neovascularization and vascular endothelial growth factor-induced breakdown of the blood-retinal barrier, Hum Gene Ther. 14 (2003) 129-41. doi:10.1089/104303403321070829.

[62] R. Rota, T. Riccioni, M. Zaccarini, S. Lamartina, A. D. Gallo, A. Fusco, et al., Marked inhibition of retinal neovascularization in rats following soluble-flt-1 gene transfer, J. Gene Med. 6 (2004) 992-1002. doi:10.1002/jgm.586.

[63] M. H. Dastjerdi, Z. Sadrai, D. R. Saban, Q. Zhang, R. Dana, Corneal penetration of topical and subconjunctival bevacizumab, Invest Ophthalmol Vis Sci. 52 (2011) 8718-23. doi:10.1167/iovs.11-7871.

INCORPORATION BY REFERENCE

All publications, patents, and patent applications mentioned in this specification are herein incorporated by reference to the same extent as if each individual publication, patent, or patent application was specifically and individually indicated to be incorporated by reference.

It will be understood that various details of the presently disclosed subject matter can be changed without departing from the scope of the subject matter disclosed herein. Furthermore, the foregoing description is for the purpose of illustration only, and not for the purpose of limitation.

The invention claimed is:

1. A method of delivering a therapeutic agent to an eye, comprising:
   administering to the eye of a subject an effective amount of a compound that comprises an elastin-like polypeptide (ELP) coupled to a VEGF antagonist therapeutic agent, wherein the ELP comprises at least one repeat of the amino acid sequence VPGXG (SEQ ID NO:1), wherein X comprises an amino acid and does not include proline.

2. The method of claim 1, wherein administration comprises one or more of topical administration, subconjunctival administration, and intraocular injection.

3. The method of claim 1, wherein a size of the ELP is configured to permit ocular penetration of the compound.

4. The method of claim 3, wherein the ELP comprises about 5 to about 300 VPGXG (SEQ ID NO:1) sequences.

5. The method of claim 1, wherein the X amino acid is hydrophilic to permit stability of the compound in the ocular environment.

6. The method of claim 5, wherein X is selected from a mixture of Val, Ala, and Gly in a 1:8:7 ratio (SEQ ID NO:2), a mixture of Val, Ala, and Gly in a 1:4:3 ratio (SEQ ID NO:3), Gly (SEQ ID NO: 4), Ser (SEQ ID NO: 5), or His (SEQ ID NO:6).

7. The method of claim 1, wherein X is hydrophobic to permit corneal penetration of the compound.

8. The method of claim 7, wherein X is selected from Val (SEQ ID NO:7), Leu (SEQ ID NO: 8), or Ile (SEQ ID NO:9).

9. The method of claim 1, wherein the compound further comprises a cell-penetrating peptide (CPP) coupled to the ELP.

10. The method of claim 9, wherein the cell-penetrating peptide is selected from penetratin, Tat, SynB1, Bac, pol-yArg, MTS, Transportan, and pVEC.

11. The method of claim 1, wherein the compound further comprises an attachment site configured to couple to the VEGF antagonist therapeutic agent, and wherein the attachment site comprises one or more Cys or Lys residues.

12. The method of claim 1, wherein the VEGF antagonist therapeutic agent is linked to the ELP with a cleavable linker to allow release of the VEGF antagonist therapeutic agent intraocularly.

13. The method of claim 1, wherein the administering of the compound further comprises treating a corneal disorder in the subject.

14. The method of claim 13, wherein the VEGF antagonist therapeutic agent is chosen from:
   a member of the sFlt-1 family,
   the-sFlt-1 protein (SEQ ID NO:10),
   sFlt-1 Ig-like domains 1, 2, and 3 (SEQ ID NO:11),
   sFlt-1 Ig-like domains 2 and 3 (SEQ ID NO:12), or a combination thereof.

15. The method of claim 13, wherein the therapeutic agent is PEDF (SEQ ID NO:13).

16. The method of claim 1, wherein the therapeutic agent is an anti-inflammatory drug, an anti-inflammatory peptide, or a combination thereof.

17. The method of claim 13, wherein the compound further comprises a cell-penetrating peptide.

18. The method of claim 17, wherein the cell penetrating peptide is selected from penetratin, Tat, SynB1, Bac, pol-yArg, MTS, Transportan, POD, and pVEC.

19. The method of claim 13, wherein the disorder is selected from the group consisting of an ocular infection and a neovascularization disorder.

20. A method of treating ocular infection or neovascular-ization in a subject, comprising:

administering to the eye of a subject an effective amount of a compound that comprises an elastin-like polypep-tide (ELP) coupled to a VEGF antagonist therapeutic agent, wherein the ELP comprises at least one repeat of the amino acid sequence VPGXG, wherein X com-prises an amino acid and does not include proline (SEQ ID NO:1);

wherein the compound forms a hydrogel after topical application or intraocular injection.

21. A method of delivering a therapeutic agent to an eye, comprising:

administering to the eye of a subject an effective amount of a hydrogel that comprises an elastin-like polypeptide (ELP) coupled to a VEGF antagonist therapeutic agent, wherein the ELP comprises at least one repeat of the amino acid sequence VPGXG (SEQ ID NO:1), wherein X comprises an amino acid and does not include proline.

22. The method of claim 21, wherein the administering step is ocular injection.

\* \* \* \* \*